US010573003B2

(12) United States Patent
Sethi et al.

(10) Patent No.: US 10,573,003 B2
(45) Date of Patent: Feb. 25, 2020

(54) SYSTEMS AND METHODS FOR COMPUTATIONAL PATHOLOGY USING POINTS-OF-INTEREST

(71) Applicants: Amit Sethi, Palatine, IL (US); Neeraj Kumar, Chicago, IL (US)

(72) Inventors: Amit Sethi, Palatine, IL (US); Neeraj Kumar, Chicago, IL (US)

( * ) Notice: Subject to any disclaimer, the term of this patent is extended or adjusted under 35 U.S.C. 154(b) by 87 days.

(21) Appl. No.: 15/894,247

(22) Filed: Feb. 12, 2018

(65) Prior Publication Data
US 2018/0232883 A1 Aug. 16, 2018

(30) Foreign Application Priority Data

Feb. 13, 2017 (IN) .............................. 201711005034

(51) Int. Cl.
*G06T 7/00* (2017.01)
*G06N 3/08* (2006.01)
(Continued)

(52) U.S. Cl.
CPC .......... *G06T 7/0014* (2013.01); *G06K 9/4671* (2013.01); *G06K 9/628* (2013.01);
(Continued)

(58) Field of Classification Search
CPC ................ G06T 7/0012; G06T 7/0014; G06T 2207/30024; G06K 2209/05;
(Continued)

(56) References Cited

U.S. PATENT DOCUMENTS 7,136,518 B2 * 11/2006 Griffin ................ A61B 5/0059
382/133
7,282,723 B2 * 10/2007 Schomacker ........ A61B 5/0059
250/458.1
(Continued)

FOREIGN PATENT DOCUMENTS

WO WO-2018115055 A1 * 6/2018 ........... G06T 7/0012
WO WO-2018165103 A1 * 9/2018 ........... G01N 33/574

OTHER PUBLICATIONS

Cosatto et al.; "Automated gastric cancer diagnosis on H&E-stained sections; ltraining a classifier on a large scale with multiple instance machine learning"; Proc. SPIE 8876, Medical Imaging 2013: Digital Pathology, 867605; Mar. 29, 2013 (Year: 2013).*
(Continued)

*Primary Examiner* — John Villecco
(74) *Attorney, Agent, or Firm* — Cygan Law Offices P.C.; Zakia Iftekhar Khan

(57) ABSTRACT
Systems, methods and devices for determination of disease class scores for patient tissue are disclosed. The disease class scores may be based on the probability or probability-like metric for a disease condition or outcome. The system includes an imaging apparatus and a computing system with instructions executable by a processor. The computer system may locate one or more points-of-interest on the pre-processed images of the patient tissue using a point-of-interest detector and generate one or more disease spatial maps including one or more probability or probability-like metric of disease classifications on the detected points-of-interest. The information in the disease spatial maps is aggregated to produce disease class scores.

20 Claims, 11 Drawing Sheets

(51) Int. Cl.
  *G06N 3/04* (2006.01)
  *G16H 50/20* (2018.01)
  *G06K 9/46* (2006.01)
  *G06K 9/62* (2006.01)
  *G16H 30/40* (2018.01)
  *G06N 20/10* (2019.01)
  *G06N 5/00* (2006.01)
  *G06N 20/20* (2019.01)

(52) U.S. Cl.
  CPC ......... *G06K 9/6267* (2013.01); *G06K 9/6277* (2013.01); *G06N 3/08* (2013.01); *G16H 50/20* (2018.01); *G06K 2209/05* (2013.01); *G06K 2209/051* (2013.01); *G06K 2209/053* (2013.01); *G06N 20/10* (2019.01); *G06N 20/20* (2019.01); *G06T 2207/10056* (2013.01); *G06T 2207/20076* (2013.01); *G06T 2207/20081* (2013.01); *G06T 2207/20084* (2013.01); *G06T 2207/30024* (2013.01); *G06T 2207/30096* (2013.01)

(58) Field of Classification Search
  CPC ............ G06K 9/00147; G06K 9/6267; G06K 2209/051; G06K 2209/053; G16H 50/20
  See application file for complete search history.

(56) References Cited

U.S. PATENT DOCUMENTS

| | | | | |
|---|---|---|---|---|
| 9,060,685 | B2* | 6/2015 | Cosatto | A61B 5/0033 |
| 9,224,106 | B2* | 12/2015 | Cosatto | G06N 20/00 |
| 9,779,213 | B2* | 10/2017 | Donovan | G16H 50/50 |
| 10,049,447 | B2* | 8/2018 | Lloyd | G06K 9/0014 |
| 10,102,418 | B2* | 10/2018 | Bredno | G06K 9/00147 |
| 10,176,579 | B2* | 1/2019 | Chukka | G06T 7/0012 |
| 10,181,180 | B2* | 1/2019 | Sarkar | G06T 5/003 |
| 10,290,101 | B1* | 5/2019 | Podilchuk | G06T 7/0012 |
| 10,430,946 | B1* | 10/2019 | Zhou | A61B 5/7282 |
| 2006/0013454 | A1* | 1/2006 | Flewelling | A61B 1/042 |
| | | | | 382/128 |
| 2010/0021031 | A1* | 1/2010 | Brockway | G06K 9/3233 |
| | | | | 382/128 |
| 2011/0280457 | A1* | 11/2011 | Nielsen | G06T 7/0012 |
| | | | | 382/131 |
| 2012/0008838 | A1* | 1/2012 | Guyon | G06T 7/0012 |
| | | | | 382/128 |
| 2013/0315465 | A1* | 11/2013 | Cosatto | A61B 5/0033 |
| | | | | 382/133 |
| 2014/0233826 | A1* | 8/2014 | Agaian | G16H 50/30 |
| | | | | 382/133 |
| 2015/0265251 | A1* | 9/2015 | Cho | A61B 8/0825 |
| | | | | 600/437 |
| 2016/0042511 | A1* | 2/2016 | Chukka | G06T 7/0012 |
| | | | | 382/133 |
| 2016/0253466 | A1* | 9/2016 | Agaian | G06N 3/0427 |
| | | | | 382/128 |
| 2016/0314580 | A1* | 10/2016 | Lloyd | G06K 9/0014 |
| 2017/0032090 | A1* | 2/2017 | Kamen | G06N 7/005 |
| 2017/0091937 | A1* | 3/2017 | Barnes | C12Q 1/6886 |
| 2017/0103521 | A1* | 4/2017 | Chukka | G06K 9/0014 |
| 2017/0193657 | A1* | 7/2017 | Madabhushi | G06N 3/08 |
| 2017/0270666 | A1* | 9/2017 | Barnes | G16H 50/30 |
| 2017/0323431 | A1* | 11/2017 | Sarkar | G06T 5/003 |
| 2017/0372117 | A1* | 12/2017 | Bredno | G06K 9/0014 |
| 2018/0114317 | A1* | 4/2018 | Song | G06K 9/6265 |
| 2018/0129911 | A1* | 5/2018 | Madabhushi | G06K 9/4628 |
| 2018/0165809 | A1* | 6/2018 | Stanitsas | G06F 3/0484 |
| 2018/0247405 | A1* | 8/2018 | Kisilev | A61B 5/0013 |
| 2018/0253590 | A1* | 9/2018 | Lloyd | G06T 7/0012 |
| 2018/0286043 | A1* | 10/2018 | Barnes | G06T 7/11 |
| 2018/0374210 | A1* | 12/2018 | Barker | G06T 7/0012 |
| 2019/0073770 | A1* | 3/2019 | Moradi | G06N 3/08 |
| 2019/0147592 | A1* | 5/2019 | Yu | G06T 7/0012 |
| 2019/0156159 | A1* | 5/2019 | Kopparapu | G06K 9/6267 |
| 2019/0325215 | A1* | 10/2019 | Wang | G06K 9/00523 |
| 2019/0340468 | A1* | 11/2019 | Stumpe | G06K 9/00134 |

OTHER PUBLICATIONS

Saito et al.; "Dawn of the digital diagnosis assisting system, can it open a new age for pathology"; Proc. SPIE 8676, Medical Imaging 2013: Digital Pathology, 867602; Mar. 29, 2013; (Year: 2013).*

* cited by examiner

SYSTEMS AND METHODS FOR COMPUTATIONAL PATHOLOGY USING POINTS-OF-INTEREST

CROSS-REFERENCE

This application claims the benefit of Indian patent application No. 201711005034 filed on Feb. 13, 2017 under 35 USC § 365.

BACKGROUND

Manual examination of tissue samples under a microscope is fraught with problems such as imprecision, inaccuracies, inter- and intra-pathologist discordance, lengthy examination times, and human inability to pick up subtle visual cues of differences in disease classes. Some communities in different parts of the globe have limited access to pathologists. On the other hand, advances in computer vision, machine learning algorithms, computer hardware technology, and computer networking technology, along with high throughput whole slide scanning technology will enable the emergence of computational pathology systems that can alleviate the aforementioned problems. With the emergence of deep learning and convolutional neural network algorithms and methods and the development of graphical processing unit (GPU) technologies, automated analysis of digitized magnified images of tissue samples will become possible.

Moreover, machine learning systems can now be trained to distinguish between not only the current disease class definitions prevalent in clinical pathology (such as benign vs. malignant, or various grades of cancer), but also between new disease class definitions that are more meaningful for treatment planning. For example, these new disease classes could be based on evidence of causes or effects of the disease such as genomic differences of diseased cells or outcome of a particular treatment or combination of treatments based on follow up data. These new disease classes may be too subtly different from each other for human pathologists to reliably recognize compared to an automated quantitative method. Use and automated recognition of such new class definitions in addition to existing disease classes used in a clinical setting may enable more personalized treatment planning for patients. This in turn will reduce side effects, discomfort, and treatment costs, and increase treatment effectiveness leading to the advancement of precision oncology.

BRIEF SUMMARY

In one aspect, described herein is a system that includes an imaging apparatus and a computing system. In some embodiments, the imaging apparatus may include a magnifying component and an image capturing component. In some embodiments, the magnifying component may be for magnifying one or more sections of a patient tissue. In some embodiments, the image capturing component may be for capturing one or more images of the patient tissue. In some embodiments, the computing system includes at least one processor, a memory, a display, a user interface and instructions executable by the at least one processor to determine one or more disease class scores for a disease condition, pathologic sub-type, genomic sub-type, tumor grade, treatment or survival outcome for the patient tissue. The instructions include (i) an image input module receiving one or more images of the patient tissue; (ii) a user input module to receive user input; (iii) a pre-processing module applying one or more mathematical functions on the images of the patient tissue to obtain one or more pre-processed images; (iv) a points-of-interest detection module locating one or more points-of-interest on the pre-processed images using a point-of-interest detector; and (v) a classification mapping module generating one or more spatial prevalence maps composed of one or more probability or probability-like metrics of multiple disease classes; and (vi) a classification aggregator module determining the aggregated class scores for each class of an image by combining probability or probability-like metrics computed in step (v) across one or more points-of-interest located in each image obtained in step (iv) using an aggregation algorithm. In some embodiments, the classification mapping module applies one or more disease classifiers to one or more points-of-interest located in step (iv) to determine the probability or probability-like metric for two or more disease classes at each point-of-interest.

In further embodiments, the points-of-interest include centers of nuclei, cells, pathogens, nerves, blood vessels, glands or boundary points thereof. In further embodiments, the points-of interest are detected at their center points or at other points closest to their centers using a point-of-interest detector such as a pre-trained neural network, a pre-trained convolutional neural network, a pre-trained recurrent neural network, a pre-trained feed-forward neural network, a pre-trained deep neural network or a pre-trained penalized logistic regression on a set of features extracted from tissue regions around the points-of-interest. In further embodiments, the computing system includes a remote server wherein the instructions executable by at least one processor are located on the remote server. In further embodiments, one or more images of the patient tissue include one or more slides of the patient tissue from the individual patient. In further embodiments, the patient tissue has been stained with one or more stains including, but not limited to, hematoxylin and eosin (H&E), Masson's trichrome, van Gieson, Reticulin, Heidenhain's azan trichrome, Giesma, Toluidine blue, immunohistochemistry (IHC) stains, etc. In further embodiments, the pre-processing module applies a stain separator function on the one or more images of the patient tissue, where the stain separator function comprises a blind deconvolution, such as sparse nonnegative matrix factorization. In further embodiments, the pre-processing module applies a normalizer function and compares the stain density map of one or more images of the patient tissue with a standard image, where the standard image has a known stain intensity value for each stain component. In further embodiments, the two or more disease classes comprise cancer types, cancer sub-types, treatment or survival outcomes, genomic sub-types, tumor grades, cancer scores or absence of cancers as determined form the assessment by human experts, genomic or proteomic sequencing of cells.

In further embodiments, the two or more disease classes comprise a disease outcome with or without treatment such as cancer recurrence, effectiveness of treatment options, effectiveness of drugs, follow-up procedures, metastasis status, mortality status, etc. In further embodiments, the disease state comprises a disease condition or an outcome. In further embodiments, the disease state comprises a stage or grade of a disease. In further embodiments, the disease state includes pathological, molecular or genomic sub-type; tumor grade, stage or spatial extent; treatment or survival outcome. In further embodiments, the aggregation algorithm is applied to disease class probabilities at all the points-of-interest located in step (iv). In further embodiments, one or more probability or probability-like metric of disease classifications is the weighted probability or entropy. In further embodiments, the metric of one or more disease classifications is the precision, recall, specificity, F1-score, receiver-operating-characteristic (ROC) or accuracy score. In further embodiments, the imaging apparatus comprises a whole-slide tissue scanning and imaging equipment and the patient tissue is fixed on one or more slides. In further embodiments, the imaging apparatus comprises a microscope with optical zoom and a camera for capturing the one or more images of the patient tissue. In even further embodiments, the at least one processor includes a graphics processing unit (GPU).

In further embodiments, the magnifying component magnifies with a 1× to 100× objective. In some further embodiments, the magnifying component comprises a microscope and the image capturing component comprises a digital camera or scanner. In further embodiments, the imaging apparatus includes a mobile device with a camera and a microscopic attachment. In a further embodiment, the imaging apparatus includes an infrared (IR), hyperspectral or multispectral scanner. In further embodiments, the instructions executable by the at least one processor includes software for image capturing or storage. In further embodiments, the software for image capturing and storage is capable of image enhancements such as contrast adjustment, image sharpening, and histogram equalization of one or more images of the patient tissue. In further embodiments, one or more images of the patient tissue comprises $(0.01 \mu m)^2$ to $(10 \mu m)^2$ per pixel.

In further embodiments, the patient tissue is fixed on a slide and the one or more images of the patient tissue are digital images of the slide. In further embodiments, the one or more images of the patient tissue comprises an RGB image stored as an m-by-n-by-3 data array that defines red, green, and blue color components for each individual pixel. In further embodiments, the one or more images of the patient tissue include color, fluorescent, hyperspectral, multispectral or confocal images. In further embodiments, the one or more images of the patient tissue comprise images of different sections of one slide with the patient tissue. In further embodiments, the pre-processing module includes stain separation of the one or more images of the patient tissue. In further embodiments, the pre-processing module includes normalization such as color, hue, saturation, image size, etc. In further embodiments, the pre-processing module includes image registration of two or more images of the patient tissue. In certain embodiments, the pre-processing module includes image processing operations such as noise removal, baseline correction, contrast enhancement, super-resolution, etc. In further embodiments, user input includes selection of images of patient tissue, pre-processing steps and parameters, image types and characteristics, tissue staining, disease classes, disease conditions or outcomes, etc. In further embodiments, the magnifying component magnifies slides with a 20× objective for a total magnification of 200×. In further embodiments, the magnifying component projects to an image sensor at $(0.25 \mu m)^2$ per pixel.

In further embodiments, the two or more disease classes include cancer types, grades, or cancer stages as determined from an assessment by human experts. In further embodiments, the two or more disease classes comprise cancer types, grades or cancer stages as determined by genetic sequencing of cells. In further embodiments, the two or more disease classes include a disease outcome such as cancer recurrence, effectiveness of treatment options, effectiveness of drugs, follow-up procedures, etc. In further embodiments, the disease classifier is one of several types of neural networks such as a feed forward, deep, convolutional or recurrent neural network. In further embodiments, the aggregation algorithm includes summation, averaging, moving averaging, etc. of the disease classifier estimated probability or probability-like metric of disease classification. In further embodiments, the aggregation algorithm is applied to a sub-set of the points-of-interest located in step (iv) based on the aggregation algorithm. In further embodiments, point-of-interest detector is applied patch-wise on the pre-processed image of the tissue. In further embodiments, the disease classifier is applied to the patches sampled around the points-of-interest located by the point-of-interest detector. In some embodiments, the metric of one or more disease classifications is the probability of a molecular sub-type of cancer as determined by genomic sequencing of cells. In further embodiments, the metric of one or more disease classifications is the probability of cancer recurrence or effectiveness of treatment options. In further embodiments, the metric of one or more disease classifications is the probability of cancer grade or pathological sub-type. In further embodiments, the instructions executable by at least one processor includes a reporting module for generating a report for the disease class scores for the patient tissue. In further embodiments, the report includes one or confidence values for each disease class.

In another aspect, a method for determining one or more disease class scores of a disease state on a patient tissue is disclosed. The method includes: (a) inputting one or more images of the patient tissue, wherein the tissue has been treated with a stain comprising one or more stain components; (b) generating a pre-processed image from the images of the patient tissue; (c) locating one or more points of interest in the pre-processed image using a first classifier; (d) generating a disease spatial map with the probability of a disease state at the points-of-interest in the tissue image by using a second classifier; and (e) aggregating the probability of the disease condition at each point-of-interest located in step (c) to obtain the disease class scores of the disease state for the patient tissue. In further embodiments, the first classifier is a nucleus detector comprising one or more pre-trained neural networks, convolutional neural networks, or recurrent neural networks etc. In further embodiments, the probability of the disease state is aggregated from two or more images of the patient tissue from the same patient. In further embodiments, the method undergoes periodic or continuous validation.

In another aspect, a non-transitory computer readable medium is disclosed. The medium having a series of instructions that, when executed by a processor, cause the processor to: (a) input one or more images of the patient tissue, wherein the tissue has been treated with a stain comprising one or more stain components; (b) generate disease spatial maps with the probability of a disease state at one or more points-of-interest by using a combined classifier into one out of two or more disease classes; and (c) aggregate the probability of the disease condition at each point-of-interest located in step (b) to obtain one or more disease class scores of the disease state for the patient tissue. In further embodiments, the one more images of the patient tissue undergo stain separation before step (a). In further embodiments, the points-of-interest are nuclei detected at or near their center points and the combined classifier determines the probability of a disease state at the detected nuclei. In further embodiments, the combined classifier is a pre-trained convolutional neural network. In even further embodiments, the combined classifier locates nuclei patch-wise on the pre-processed image and classifies the detected nuclei into two or more disease classes.

BRIEF DESCRIPTION OF THE DRAWINGS

Embodiments of the present invention are described with reference to the following drawings for exemplary purposes only. In the drawings, like reference numerals refer to like parts throughout various figures unless otherwise specified.

For a better understanding of the presently disclosed subject matter, reference will be made to the following Detailed Description, which is to be read in association with the accompanying drawings, wherein.

DETAILED DESCRIPTION

Figure 1A:
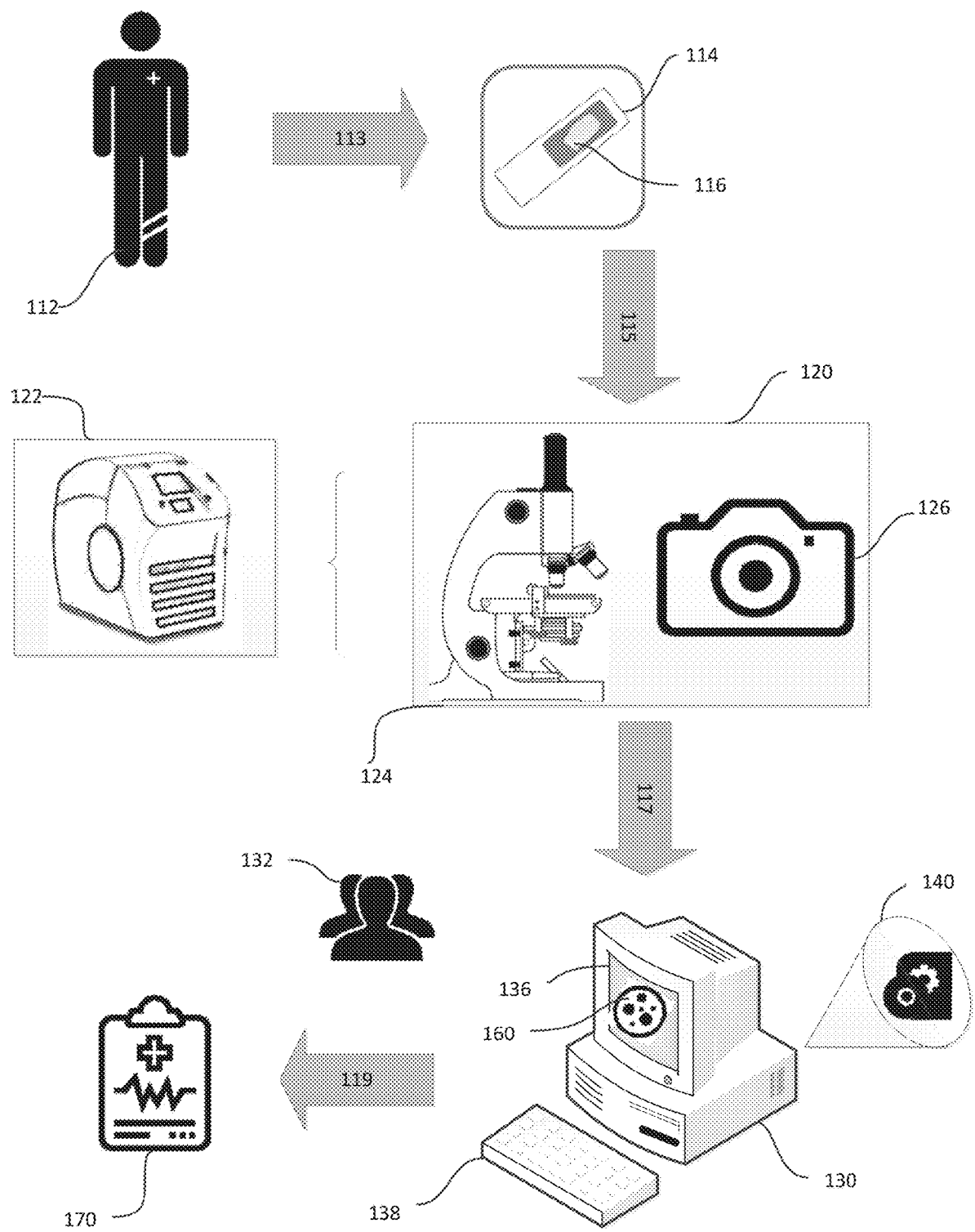
FIGS. 1A & 1B are illustrations of embodiments of the system for determining disease class scores for a disease state.

Different embodiments of this invention may allow health professionals and patients with diagnosis, prognosis, and treatment planning for diseases, such as cancers. The present invention has the potential to advance the state of computational pathology by making it more accurate, objective and efficient than current techniques. To aid personalized treatments and precision medicine, determination of specific sub-types and combinations of sub-types of cancers in patients based on their causes or likely future course may be necessary. While these sub-types may be determined from molecular tests such as genomic or proteomic testing, such testing is expensive, time consuming, often fraught with sampling issues due to sampling of only a few cells, and is devoid of spatial context such as the distances between various cell types. Computational pathology may be able to determine more refined sub-types of cancers and their co-occurrences in patients by analyzing their spatial context to help make personalized treatment recommendations in the context of precision oncology. Further, computational pathology may also determine whether a patient will respond or not to a particular treatment by objective analysis of the patient tissue sample.

Presently, while assessing tissue images in computational pathology, a common method is to assess all possible sub-images of a certain fixed size that can be obtained from patient tissue images one-by-one, and averaging the decisions made on each individual sub-image. Some techniques also apply heuristics using domain knowledge to obtain sub-images of a certain fixed size from the patient tissue. Several of these sub-images present almost no new information because of their overlap with other sub-images, which increases computational time and reduces accuracy by increasing the learning burden of the sub-image classifier used to assess them.

One or more embodiments of the present invention involve pre-processing the tissue images to remove unwanted variations across images. For example, the tissue images taken at multiple labs may reduce the accuracy of disease classifiers due to unwanted differences in training and testing images obtained from different labs. Using pre-processing, some of these unwanted variations may be normalized between training and testing images, which will increase the accuracy of the subsequent classifiers. Most importantly, we propose detecting points-of-interest (POIs) in pre-processed tissue images to focus further investigation. In the present invention, POI detection is followed by estimation of probability of each disease class at every POI. This local disease classification of each POI across one or more tissue images of a patient is combined using sophisticated aggregation along with potentially other patient data such as serum or genomic test results, to produce consolidated disease class scores.

The disease class can itself be defined in a multitude of ways. If the disease class is defined as simply cancer grades, stages or molecular subtypes, in line with current clinical diagnostic practices, then such a system can automate triage, diagnosis, or second opinion by being fast, objective, accurate, or precise. It can also potentially use a cheaper modality such as hematoxylin and eosin staining instead of the more expensive immunohistochemistry or fluorescent in-situ hybridization (FISH) to make the same diagnosis. Additionally, disease states may also be defined based on treatment or survival outcomes determined by following up with the patient for a certain length of time, thus using the technique to predict treatment outcome or survival at the time of tissue sample extraction (e.g., initial biopsy) right before treatment planning. In such an embodiment, the invention may facilitate more precise treatment planning based on predicting outcome of various treatments on the patient whose tissue is being examined.

Pre-processing, POI detection, and aggregation of local disease classification, each can have various embodiments, of which we show a limited sample in more details. In some embodiments, pre-processing can lead to color normalization, in others it can lead to relative stain density estimation or even noise removal and contrast enhancement. In some embodiments POIs may be centers or points to close to centers of all nuclei, in other cases these can specifically be epithelial nuclei, stromal nuclei or gland centers. In other embodiments, POIs may be the points along the nuclei or gland boundaries. Aggregation, similarly, may be averaging of local classifications or a more sophisticated analysis of neighborhoods to also assess confidence in local classifications based on concordance of local disease classifications of the neighboring POIs. In some embodiments, we have focused the nucleus detection at or near the center of the nucleus instead of defining the edges (even though edges are easier to detect) because we found that surprisingly, this gave higher accuracy in local disease classification.

Definitions

As referenced herein, the term "patient tissue" refers to a section of tissue with biological constituents such as cells, cytoplasm, etc. obtained from a human or animal subject that is being assessed for evidence of diseases such as cancers. Further, we use the term to also mean tissue samples prepared for examination on slides, and treated with stains such as H&E, Masson's trichrome, van Gieson, Reticulin, Heidenhain's azan trichrome, Giesma, Toluidine blue, immunohistochemistry (IHC), Feulgen etc. to either enhance the contrast between various tissue components, or to indicate the presence of certain types of compounds such as specific proteins or other biomarkers in the tissue. As referenced herein, the term "health professionals" refers to medical doctors, pathologists, oncologists, surgeons, clinicians and other people involved in decision-making about patient disease prevalence, recommending and administering treatment, and following up on disease progression and treatment or survival outcome.

As referenced herein, the term "image" refers to an arrangement of pixel values on a 2-dimensional grid of rows and columns. In addition to the two dimensional grid, a third dimension may also represent spectral bands, such as red, green, and blue for color images, or a multitude of bands of the electromagnetic spectrum for multi- and hyper-spectral images. We use the terms "bands" and "channels" interchangeably.

As referenced herein, the term "disease class" or "disease classifications" or "disease condition" or "disease outcome" refers not only to the histologic diagnostic definitions prevalent in current clinical pathology such as benign vs. malignant or various grades of cancer, but also new disease class definitions that may be more actionable and meaningful for treatment planning. These new disease classes at the time of their determination could be based on evidence of causes of diseases such as genomic differences of diseased cells, or on their histological or other evidence linked to future course of disease with or without a specified treatment such as "will become metastatic within 1 year even after the treatment in question" vs. otherwise, or "will recur within 3 years even after the treatment in question" vs. otherwise, or "will lead to mortality in 5 years" vs. otherwise. Such future outcomes may be determined based on patient follow up after the treatment.

As referenced herein, the terms "probability metric" or "probability-like metric" refers to a number that can take any value between a low and a high end of a continuous or discrete number range. We use this number to represent the likelihood of a particular disease class. As referenced herein, the term "classifier" or "machine learning framework" refers to sequence of mathematical and logical operations on an input to estimate probability or probability-like metric for each class from a particular set of classes. As referenced herein, the term "disease classifier" refers to a classifier that estimates a category or probability or probability-like metric of the existence of each disease class from a particular set of disease classes.

As referenced herein, the term "neural network" or "feedforward neural network" refers to a mathematical framework to model a complicated function using a network of simpler functions represented by nodes, where the nodes are arranged in layers. Such a framework has an input layer, at least one hidden layer, and an output layer. Each node has a single output, which acts as an input to the nodes in subsequent layers away from the input and towards the output. When the output of node A acts as an input to node B, it is said that A is connected to B. Each connection between nodes has an associated multiplicative factor called weight, which is tuned using an optimization algorithm known as a learning or training algorithm to iteratively move the output of the neural network closer to that of a desired output. The neural network is trained using training data while the optimization performance during training is measured by computing the errors between the neural network output and the desired output using an error function. The architecture of the neural network, that is, the number of hidden layers and nodes in each layer is selected by evaluating the performance of multiple trained neural network architectures on validation data. As referenced herein, the term "convolutional neural network" refers to a type of neural network having an input layer, at least one convolutional layer, plurality of densely connected layers and an output layer with each layer having one or more nodes (input, dense, and output layer) or filters (in convolutional layers) with or without connections that skip layers or feed the same layers.

As referenced herein, the term "deep learning" refers to a type of machine learning where the relationship between training input-output pairs is learned in terms of hierarchical model composed of plurality of intermediate layers which extract increasingly complex features as the information flows from input to the output. Examples of deep learning models include, but are not limited to a deep convolutional neural network, a deep belief network, a recurrent neural network, an autoencoder, etc. As referenced herein, the term "parameters" refers to a set of numbers that determine the behavior of a classifier, such as the weights of connections in a neural network, which are determined using an automated tuning or numerical optimization operation known as "training". As referenced herein, the term "training" refers to a process of using training data and validation data to tune or set the parameters of a classifier using numerical optimization such that the classifier gives a desirable level of performance on these data as determined by a set measure of performance such as "average accuracy of classification on validation data."

As referenced herein, the term "hyper-parameters" refers to design choices of a classifier that are pre-set before training, such as the number of layers of a neural network. As referenced herein, the term "training data" refers to a set of inputs paired with their corresponding ideal classifier outputs, and used for training a classifier. As referenced herein, the term "validation data" refers to a set of inputs paired with their corresponding ideal classifier outputs, and used for evaluating a classifier's performance including the choice of the classifier's hyper-parameters. As referenced herein "validation" refers to the process of confirming the level of confidence in the results from the invention. In some cases, validation may be conducted continuously or periodically based on established standards such as those established in the field of endeavor or as required by government or FDA regulations.

As referenced herein, the term "training process" refers to the process of setting a set of hyper-parameters of a classifier, training the classifier using training data, evaluating the classifier using validation data, changing the hyper-parameters if necessary before training the classifier again. As referenced herein, the term "testing data" refers to a set of input data whose ideal output is unknown at the time of using a machine learning framework that is learned using training. The desired output of the input associated with the testing data may be revealed at a later time, at which it can be included in the training or validation data or can be used to evaluate the performance of a trained classifier.

As referenced herein, the term "computing device" refers to a device containing at least one central processing unit, a random access memory, and a non-volatile memory, capable of executing instructions from an instruction set. As referenced herein, the term "computing system" refers to one or more computing devices such that different computational modules may reside and execute their instructions on different computing devices of this computing system, and exchange data between computing devices using communication links such as local area networks, internet, or wireless network. Cloud computing is an example of such a computing system where client computers send input data and commands to one or more server computers located remotely on the internet to execute those commands and send the results back to the client computer for reporting and display. In such cases, certain computing devices do not have their own user interfaces or display, such as the servers in the cloud, and only the client computers do.

As referenced herein, the term "instructions executable by the at least one processor" refers to a series of instructions that encode a set of operations applied to digital data such as images and at least one processing unit capable of executing these programming instructions. As referenced herein, the term "mathematical functions" refers to a set of functions including, but not limited to, matrix multiplication, addition, exponentiation, linear scaling etc. that can be applied to digital data using a computing device.

As referenced herein, the term "pre-processed image" refers to a digital image that has been processed by the application of one or more mathematical functions to transform image pixels into more useful form such as a color normalized image, or a reduced channel image, such that it is advantageous for certain modules in terms of accuracy or computational or memory requirements to work with the pre-processed image instead of the original image that has not been pre-processed.

As referenced herein, the terms "sub-image," "patch," and "window" refer to usually a rectangular (usually square)-shaped topologically contiguous subset of pixels of an image where its shape and size is fixed based on the spatial context that is deemed sufficient for making certain decisions about one or more pixels contained within it. The shape of the window can also be something else such as a circle or ellipse. As referenced herein, the term "point-of-interest" (POI) or "points-of-interest" (POIs) refer to location or a subset of locations in a tissue image that are believed to yield a richer set of information about disease classes from windows centered at the POIs compared to the windows that do not contain POIs. Examples of POIs include centroids or points close to the centroids of epithelial or stromal nuclei, medoid of luminal cavities, gland centers or points along the gland, blood vessel, bone or nuclei boundaries etc.

As referenced herein, the term "points-of-interest detector" or "POI detector" refers to a sequence of operations applied onto a tissue image or a pre-processed tissue image to identify points-of-interest. Examples of point-of-interest detector may be convolutional neural network based nuclei, gland, bone or blood vessel detector. As referenced herein, the term "disease probability map" or "spatial map of probability" refers to a map obtained on a discrete sampling grid (such as image pixel locations) by arranging the quantitative measure of disease condition, such as probability or a probability-like metric, for each pixel in a tissue image into respective discrete locations.

As referenced herein, the term "aggregator" refers to a method of combining multiple probability or probability-like metric from different POI locations from one or more tissue images of the same patient using certain mathematical functions such as averaging, majority voting, or examination of concordance in the spatial neighborhood, etc. As referenced herein, the term "graph" refers to a mathematical concept in which there is a set of nodes or vertices, connected by a set of edges. An edge represents a pair of vertices that are connected to each other. A "nearest neighbor graph" is a graph in which a set of points in a Euclidean space are treated as vertices, and the edges exist between any point and its nearest k Euclidean neighbors, where k is a pre-specified number, usually around 5.

FIG. 1A is an illustration of an exemplar embodiment of the system for determining disease class report for a disease condition or outcome. As shown, patient tissue 116 from a patient 112, such as a human or non-human, may have been collected for diagnosis, treatment or other reasons. The tissue 116 may be treated with standard techniques known in the art, such as stained and fixed on a slide 114.

One or more users 132 using the imaging apparatus 120, 124 may view the slide 114 with patient tissue 116. In certain embodiments, the imaging apparatus includes a magnifying component 124 and an image capturing component 126. The magnifying component 124 may be capable of producing a magnified view of the tissue such as a microscope. The magnifying component may include an illuminator, focusing components, plurality of eyepiece and objective lenses, etc.

The image capturing component 126 may be able to capture a magnified tissue image 160 and store onto a non-transitory computer readable medium 162 (not shown). The image 160 may be stored onto a computing device (e.g., 130) in direct or indirect communication with the imaging apparatus 120.

In a preferred embodiment, the imaging apparatus 122 includes both a magnifying and image capturing component. For example, the imaging apparatus 122 may be capable of magnifying and scanning an entire slide, referred to as whole slide image (WSI) scanner. The WSI scanner may include the following components: i) a microscope with one or more objective lenses, ii) light source (bright field and/or fluorescent sources), iii) robotics to automatically load and move glass slides, iv) one or more digital cameras for image capturing, v) a computer, and vi) software to manipulate, manage, and view digital slides. Some WSI devices may have dynamic pre-focusing functionality by utilizing one camera to focus and another for scanning.

In some embodiments, a computing device 130 may be used for storing and viewing one or more images 160 of the patient tissue 116. The computing system may include one or more processors 132, a memory 134, a display 136, a user interface 138, and other computer components. The computing device may be loaded with instructions executable by the processor, such as an application 140. The application 140 may be saved locally on the hard drive (as shown) of the computing device 130 or may be accessible on a remote server or cloud-based system. The image 160 may be analyzed using the application 140 and the results may be displayed on the display 136 for one or more users 132 to view. In addition, the application 140 may prepare a report 170 to describe the results.

Figure 1B:
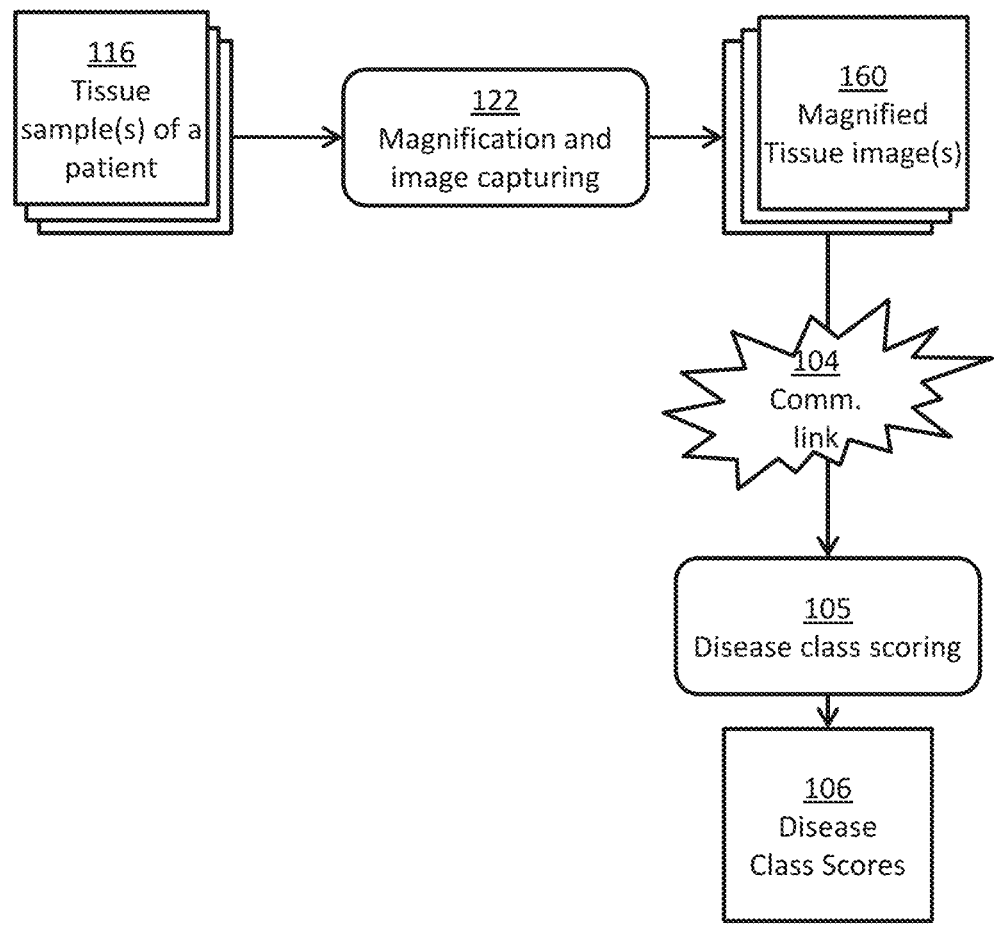

FIG. 1B is an illustration of an exemplar embodiment of the system for determining disease class scores for a disease condition or outcome. Here, the patient tissue 116 undergoes magnification and image capturing using the imaging apparatus 122 and the magnified tissue image(s) 160 is (are) transferred through communication link 104 to a disease class scoring module 105 to generate disease class scores 106.

In a preferred embodiment, patient tissue 116 is a hematoxylin and eosin stained tissue of a human or non-human patient, and the imaging apparatus 122 may include a WSI scanner to generate magnified tissue WSI(s) 160. The communication link 104 may be a wired connection, such as through a universal serial bus, between the imaging apparatus 122 and a disease class scoring module 105, or it could be a communication link over the internet. The disease class scores 106 may contain an assessment of disease condition, prediction of treatment outcome, disease spatial extent, and confidence in disease classes or their spatial extents in a digital file.

In some embodiments, patient tissue 116 may be stained with immunohistochemical stains or fluorescent antibodies, and the imaging apparatus 122 may include at least one brightfield, fluorescence or FISH scanner. Additionally, the imaging apparatus 122 may be a multispectral or hyperspectral scanner capable of capturing tissue images at several spectral frequencies across the electromagnetic spectrum. In certain embodiments, the communication link 104 may include an Internet enabled wired or wireless connection between a remote imaging apparatus 122 and a computing device 130.

Figure 1C:
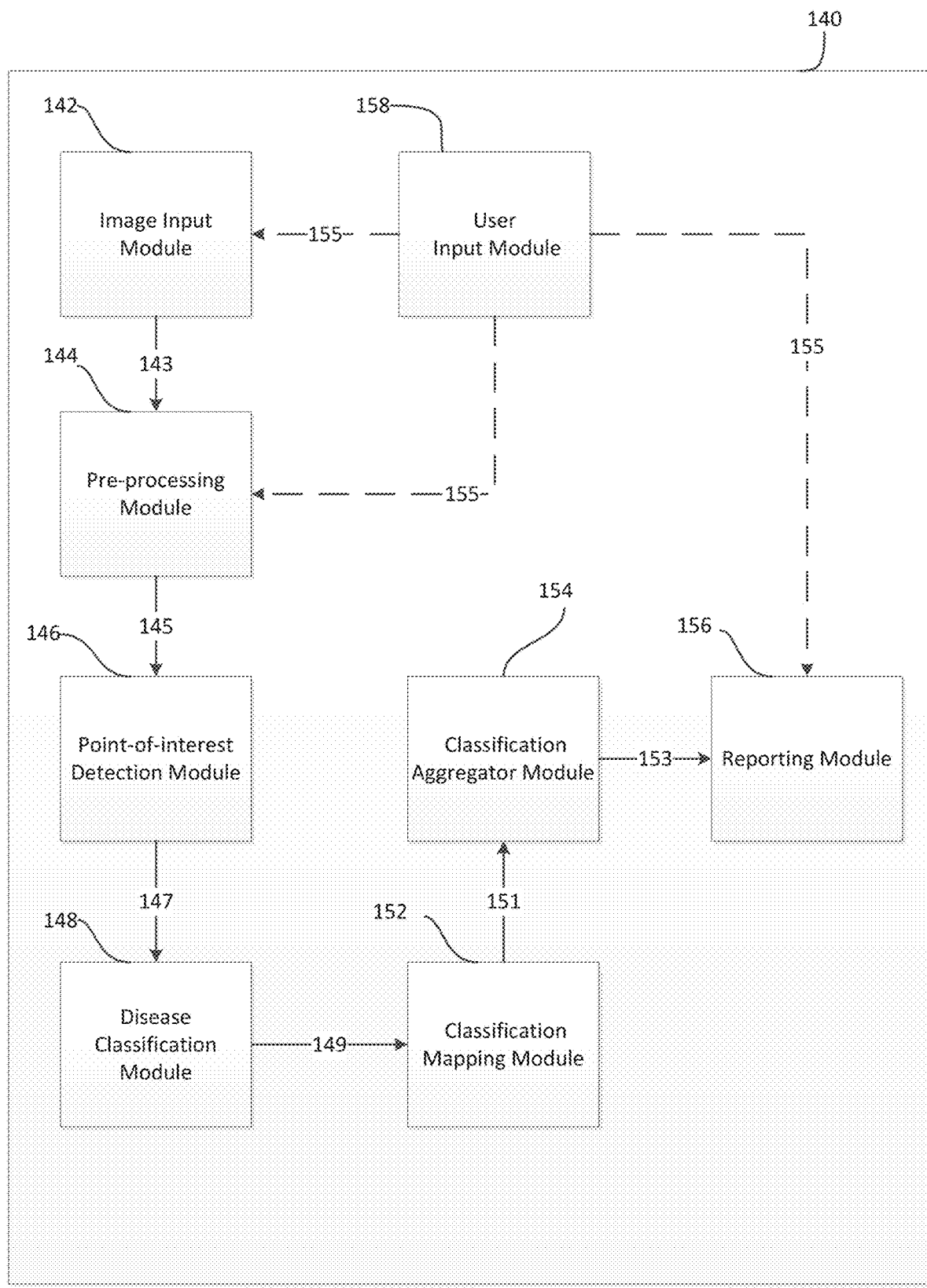
FIG. 1C is an illustration of instructions executable by at least one processor to determine disease class scores of a disease state for the patient tissue.

FIG. 1C is an illustration of the series of operations applied on magnified tissue image(s) 160 by at least one computing device 130 to produce a disease class report for disease condition or outcome (or disease state) for one or more patient tissue. As shown, the application 140 may include an image input module 142 for receiving one or more images of the patient tissue 160 (not shown). The images 160 may be pre-processed using the pre-processing module 144 to generate one or more pre-processed image(s) 164 (not shown). The pre-processed image 164 (not shown) may be inputted into the point-of-interest (POI) detection module 146 for locating points-of-interest 166 (not shown). Next, the disease classification module 148 may generate one or more local disease classifications 167 (not shown) that contain one or more probability or probability-like metric for each disease class at every POI. In certain embodiments, one or more disease classifiers are applied to plurality POIs identified by POI detection module 146. In certain embodiments, the absence of a disease can be one of the disease classes.

In some embodiments, a Classification Mapping Module 152 may take the local disease classifications 167 (not shown) to produce a disease class map 169 (not shown) utilizing the pixel location of the POI associated with each local disease classification. A classification aggregator module 154 may determine one or more disease class scores 172 (not shown) (also referred to as the "overall probability or probability-like metric") for all disease classes for each patient 160 by combining probability or probability-like metric computed across the one or more points-of-interest located in plurality of image using an aggregation operation. The classification aggregator module 154 may also calculate the level of confidence in the results based on spatial concordance or other metric described in FIG. 6.

A user input module 158 may receive user input 155 for one or more aspects of the analysis. For example, user may instruct the image input module 142 to receive multiple modalities of tissue image(s) 160 such as hematoxylin and eosin stained, immunohistochemistry stained, multispectral and hyperspectral images of the same patient tissue. In addition, user can select from multitude of pre-processing operations including, but not limited to, noise removal, baseline correction, contrast enhancement and color normalization for plurality of tissue images based on the type of imaging modality received by the image input module 142. Furthermore, a user can instruct the reporting module 156 to use the disease class scores 172 (not shown) to prepare a report in a format desired by health professionals or users with additional information such as patient name and other medical test results and send the reports to one or more experts as a digital document attached in an email or to a remote server for saving the patient report. The user can also instruct the POI detection module 146 and the disease classification module 148 to detect POIs relevant to a particular set of disease classes and determine their probability at each detected POI.

It is understood that any of these operations may take place on a separate computing device. For example, the flow of data as illustrated by 143, 145, 147, 149, 151, 153, 155 may be done separately through wired or wireless communication links such as the internet or a local area network.

Figure 2:
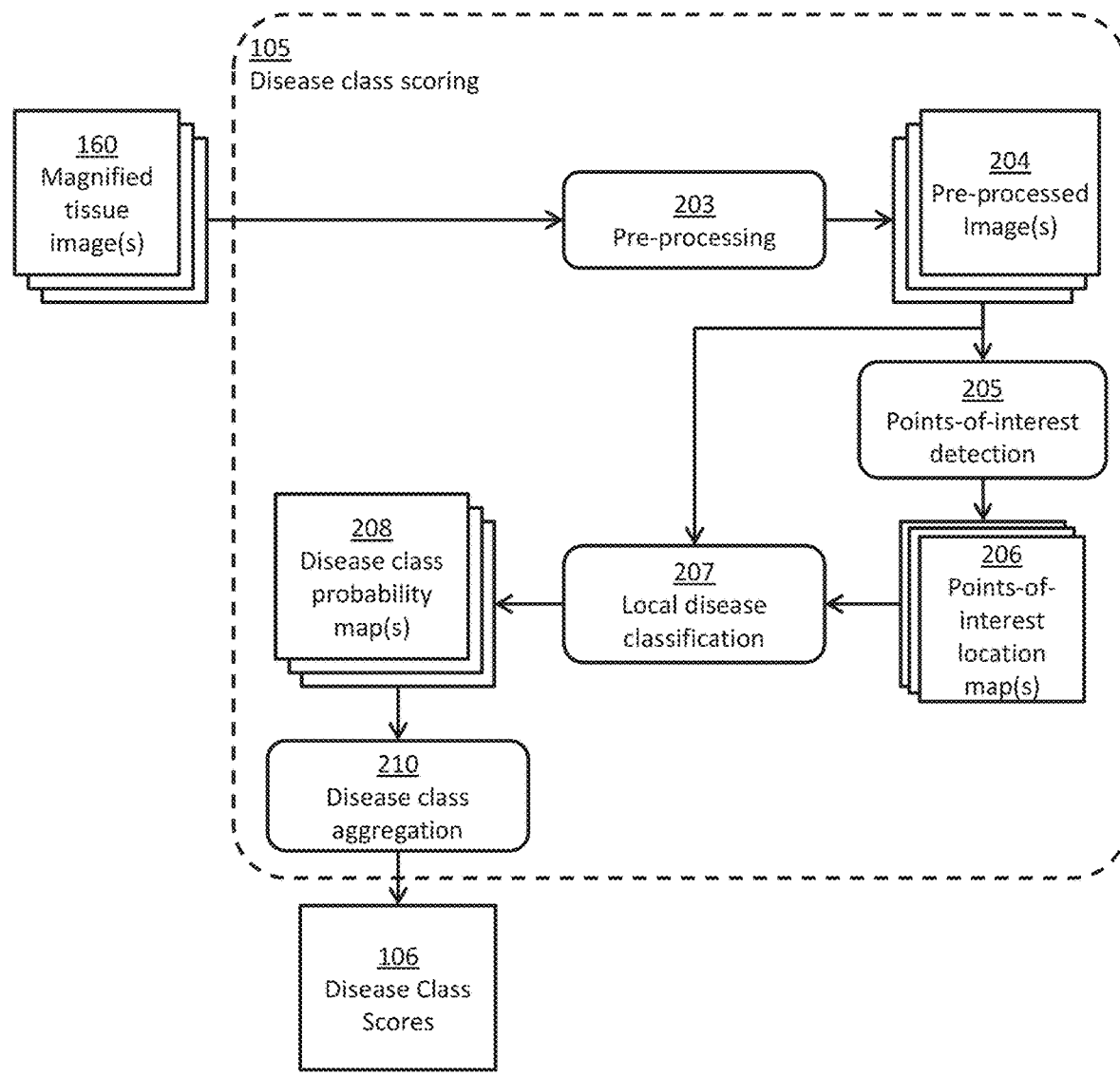
FIG. 2 is an illustration of an exemplary method for determining disease class scores for a disease state.

FIG. 2 is an illustration of parts of an exemplary method 105 to generate disease class scores 106. The objective of this method is to take patient tissue images and automatically analyze them to produce disease class scores that can be used for diagnosis, prognosis, or treatment planning. The input to the disease class scoring reporting method 105 may include one or more magnified tissue images 160 captured at a specified magnification level with one or more channels, such as red, green, and blue for color images or multiple spectral bands for hyperspectral images, which are stored in memory of a computing device. In certain embodiments, the input images 160 can reside in a separate memory than the one hosted in the computing device or system such as a cloud server that also hosts the disease class scoring module 105. In such a case, the input images 160 can be transferred over a communication link such as the internet or a local area network or a wireless connection 104 (not shown), or even be copied and physically brought to the computing device or system hosting the disease class scoring module 105.

The digitized tissue images 160 may be inputted into a pre-processing module 203 which is a part of the disease class scoring module 105. The pre-processing module 203 may output a set of pre-processed images 204 at its output. The pre-processing module 203 may account for variations in the tissue image appearance and transforms it to facilitate further processing. Various embodiments and implementations of a pre-processing module 203 consistent with spirit of this disclosure are possible. The pre-processing module 203 can include other image processing operations such as histogram equalization, noise removal, baseline correction for hyperspectral images, reduction or increase in spatial resolution, computation of hyperspectral endmembers, etc. Pre-processed images 204 at the output of pre-processing module are intended to gain advantages over working directly with input images 160 such as an increase the accuracy of other modules or a reduction in computational or memory requirements.

The pre-processed tissue images 204 may be passed into a points-of-interest (POI) detection module 205 for further processing. The POI detection module 205 may apply various operations on the pre-processed images 204 to identify the spatial coordinates, for example (x,y) locations in the Euclidean plane, of POIs. The identified POIs can be of clinical importance in examination such as nuclei or gland centers, points along the boundaries of nuclei, glands, blood vessels or bones, or could be of perceptual significance, or other points determined to be important for detailed examination along with the spatial context of pixel patterns around those points for morphometric assessment. POI location maps 206 containing spatial locations of the POIs are the output of the POI detection module 205. The POI detection may lead to advantages such as reduction in computational requirements of local disease classification module 207 which will now have to process a smaller number of pixels, and increases the accuracy of disease classification by eliminating uninformative and distracting points from being examined further.

Pre-processed images 204 along with their associated POI location maps 206 may be passed as input to the local disease classification (LDC) module 207. LDC module 207 applies a series of image processing and classification operations to compute local disease class probability map for every pre-processed input image using its POI location map. To do so, LDC module 207 may first extract sub-images (also known as windows or patches) of one or more sizes centered at the locations in the POI location map 206. Using multiple windows of different fixed sizes allows the LDC module 207 to analyze visual cues at different spatial scales, such as at the nuclear level and the glandular level.

Additionally included in the LDC module 207 may be a classifier that estimates the probability of occurrence of each disease class for the input sub-image windows of different sizes. The classifier applies multiple operations to estimate disease probability for each POI location by identifying various visual cues present in differently sized sub-image windows, extracted around each POI location, on the basis of their respective pixel arrangements. In certain embodiments, a probability-like metric can also be used instead, such as a scale from 0 to 10 instead of the probability scale of 0 to 1 as the output of classifier. In certain embodiments, the local disease classification can be done by a convolutional neural network, or another image processing and pre-trained machine learning module such as a penalized logistic regression model using features such as texture, color, gradient magnitude and direction, entropy of gradient directions etc. extracted from the differently sized sub-image windows as input. The parameters determined or learned during the training process can be internally stored on the computer hosting the disease class scoring module 105, or be brought in via a communication link such as the internet at the time of computation of the output disease class probability maps 208. The output disease class probability map 208 may store the probability of each disease at each POI location in the POI map 206.

The disease class probability maps 208 at the output of LDC module may be inputted into aggregation module 210 that combines disease occurrence probabilities of multiple POI locations for each image, in the set of input images 160, to produce consolidated disease class scores for the patient 106. In certain embodiments, the aggregation module 210 may compute the severity, extent, or confidence scores, or combinations thereof for each disease class for all the input images of a patient 160 taken together as a whole. A simple example of aggregation is averaging of disease class probabilities across all POIs of all input images of a given patient. In other embodiments, more sophisticated aggregation techniques such as computing confidence in local disease classification at each POI 208 by assessing concordance with its neighboring POIs can also be done. The aggregation module 210 thus produces disease class scores 106 that may inform diagnosis, prognosis, and treatment choices for a patient with possible modifications incorporated by a user or by integration with another system such as a disease genomic or proteomic testing-based disease class scores 106. Any of the modules described herein can reside in a separate computer than others, such that their inputs are supplied to them via a communication link such as a local area network or the internet.

Figure 3:
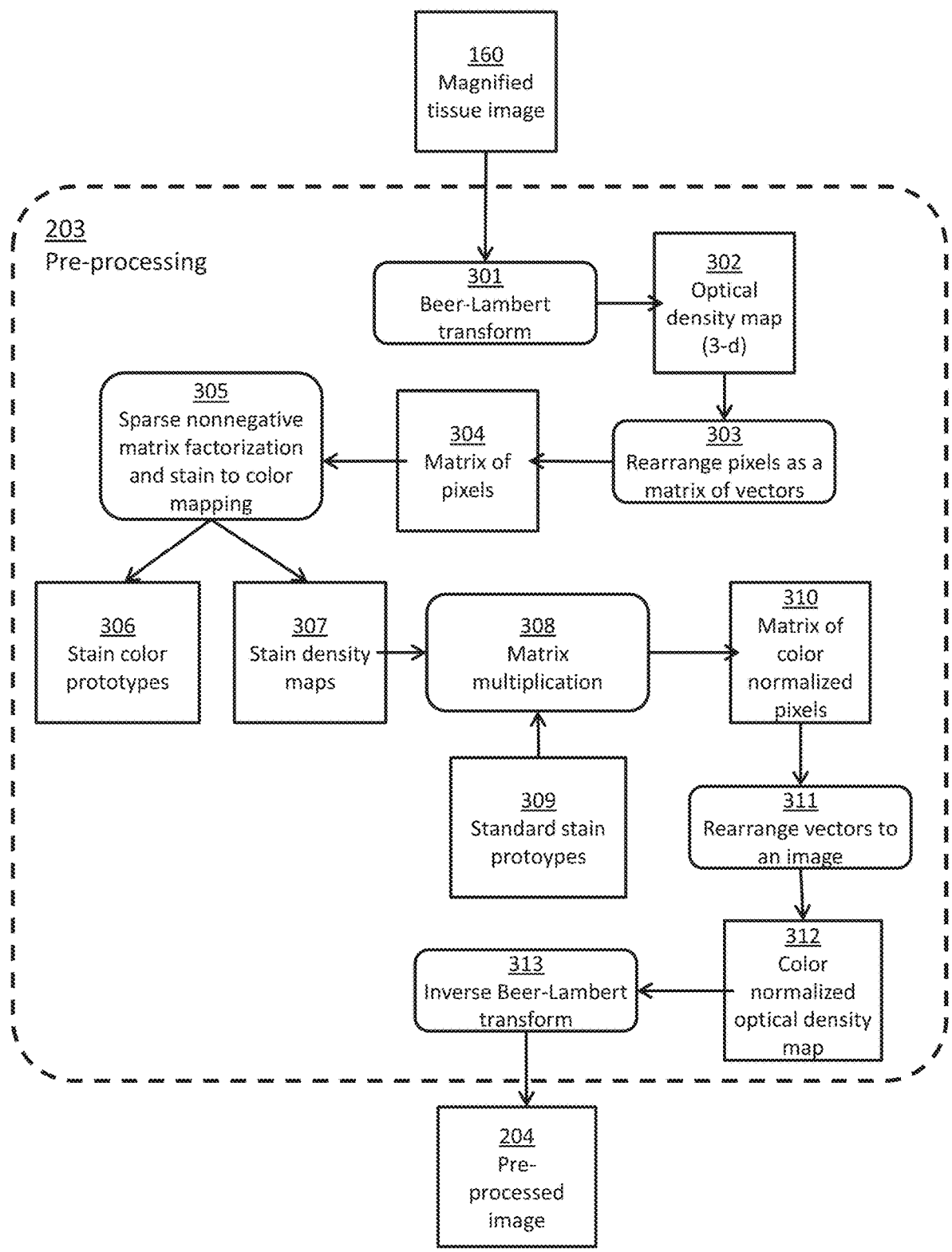
FIG. 3 is an illustration of a portion of an exemplary method for determining disease class scores for a disease state.

FIG. 3 is an illustration of an exemplary method for pre-processing magnified tissue images. The objective of using a pre-processing module 203 is to take a magnified tissue image 160 and produce a pre-processed image 204 such that it is advantageous for the other modules such as points-of-interest detection 205 or local disease classification 207 to work with the pre-processed image 204 as compared to the magnified tissue image 160. The advantage could be higher accuracy, or lower computational or memory requirements.

In some embodiments of pre-processing module 203, unwanted color variations across images taken in different settings such as staining times, reagent concentrations or brands may be normalized so that the pre-processed image uses the same color prototypes for different stains as that of a standard image, wherein standard image is pre-selected by a human expert. An example is shown in FIG. 3.

The input 160 may include one or more magnified tissue images and each image may be represented as a three-dimensional (3-d) array of pixels. The first two dimensions are columns and rows of pixels, while the third dimension is the spectral information. For color images, the third dimension has red, green, and blue spectral components, while multi-spectral and hyper-spectral images can have more than three components. Thus, each pixel represents intensities of red, green, or blue spectra for a color image, and additional spectral information for other images.

In certain embodiments as shown in FIG. 3, the input may be converted from pixel intensity to optical density map 302 via an operation that calculates Beer-Lambert transform 301. For the most widely used range of pixel values from 0 to 255, Beer-Lambert transform calculates red optical density R from red spectral intensity r as follows: $R=-\log(r+1)/(255+1)$. Similarly, it calculates optical density for blue and green channels, i.e. B and G. This optical density is also arranged as a 3-d array, known as the optical density map 302. The optical density map 302 is rearranged into a 2-d matrix of pixels 304 via a re-arrangement operation 303 such that spectral values R, G, B of each pixel forms a complete column of the matrix. The matrix of pixels 304 may be decomposed into two matrices—stain color prototypes 306, and stain density maps 307—such that both are nonnegative and their product approximates the matrix of pixels, via a sparse nonnegative matrix factorization and stain to color mapping operation 305. Additionally, the stain density map matrix is sparse such that it is highly likely for only one of the entries in a column to be nonzero. The non-zero entries represent specificity of one of multiple stains that was absorbed by the biological structure represented by that pixel location. Consistent with the spirit of this disclosure, this operation may use an optimization routine such as alternate least squares, multiplicative updates, etc.

The stain color prototypes 306 may be discarded, while the stain density maps may be combined using a matrix multiplication operation 308 with corresponding standard color prototypes (one for each R, G and B channel) 309 and concatenated to give a matrix of color normalized RGB pixels 310. The matrix of color normalized pixels 310 may be expected to look more like pixels of a standardized image (not shown) which may be used to obtain the standard color prototypes 309 in an operation outside of this system. The standard color prototypes 309 may be copied into this module via a communication link or through a memory read operation. The color normalized optical density matrix 310 is rearranged into a 3-d array 312 where the first two dimensions correspond to rows and columns of the input image 160, and the third dimension corresponds to spectral bands, using a rearrangement operation 311. Using the color normalized optical density map 312 as input, an inverse Beer-Lambert transform operation 313 produces the color-normalized image 314.

Other embodiments of the pre-processing module 203 are also consistent with the spirit of this disclosure. For example, the pre-processing may estimate optical densities of different stains, and the stain density maps 307 themselves could be the output of the pre-processing module 203. In other embodiments, a different imaging modality such as hyper-spectral imaging could produce the magnified tissue image 160. In such a case, the pre-processing could involve steps to determine spectral endmembers of the hyper-spectral image. Other pre-processing steps such as contrast enhancement, noise removal, baseline correction, or normalization of pixel value ranges or sharpening filtering etc. are also consistent with the spirit of this disclosure so long as it is advantageous for the POI detection module 205 or local disease classification module 207 to use pre-processed images 204 instead of magnified tissue images 160.

Figure 4:
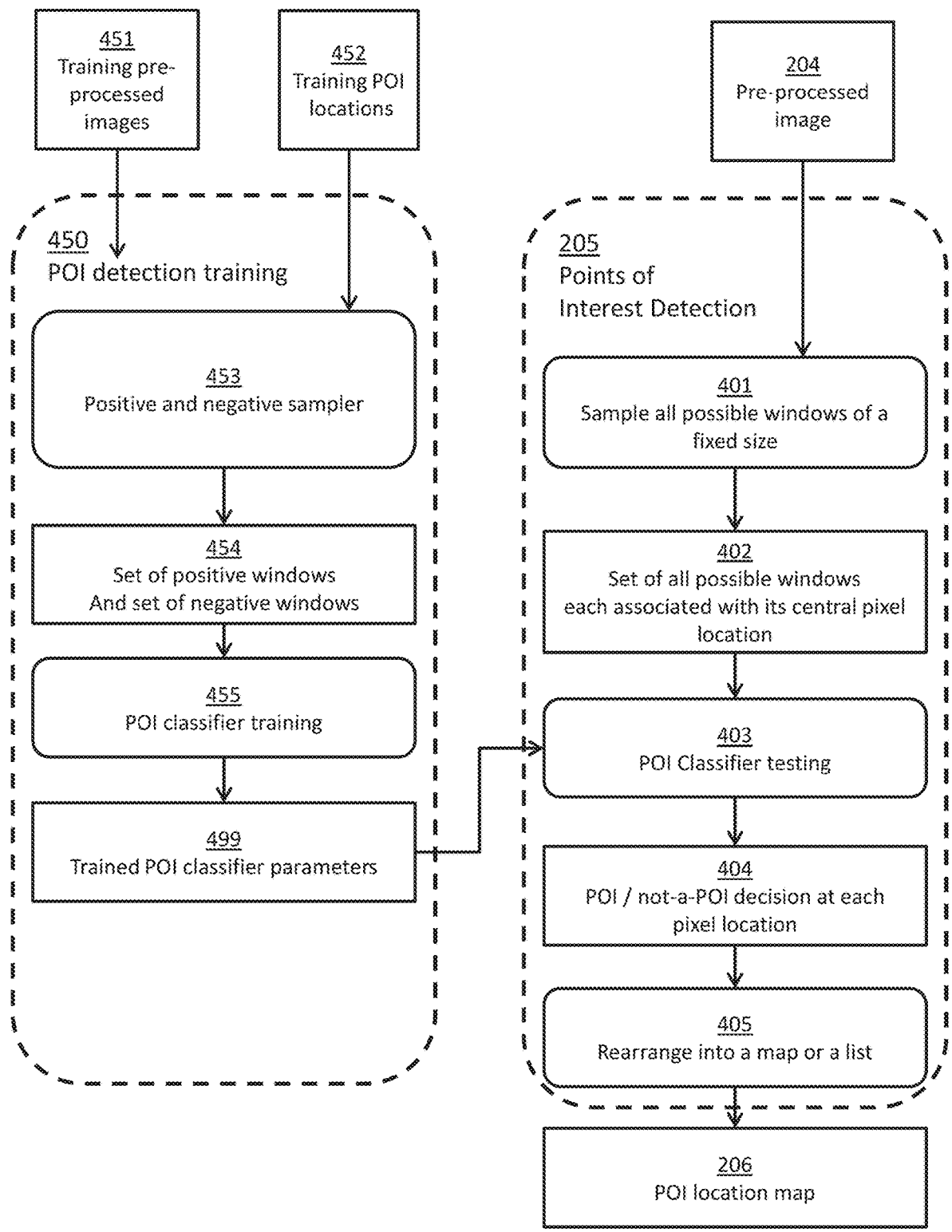
FIG. 4 is an illustration of an exemplary method for detecting points-of-interest (POIs).

FIG. 4 is an illustration of an exemplary method for detecting points-of-interest (POIs), specifically a POI detection module 205. The pre-processed images from a patient 204 are input one by one into the POI detector 205 to produce POI location maps 206.

In one embodiment, the pre-processed image 204 is input into a module 401 that samples all possible sub-image windows of a fixed size to produce a set of windows 402 associated with their central location identified as for example by (x,y) coordinates in the pre-processed image 204. The sub-image windows in this set may be inputted one by one into a POI classifier testing module 403 whose output is a list of decisions 404 about whether or not the sub-image window is a POI. To make this decision, the POI classifier testing module may use a set of parameters 499, which may be stored on the same computing device that stores the POI classifier testing module 403, or communicated to it through one of several types of communication links or data transfer mechanisms. The parameters 499 may be obtained using a module for POI detection training 450. The location of the central pixel of each sub-image window that was decided to be a POI is input into a module to rearrange these locations onto a 2-d grid or a list 405 to produce a POI location map 206.

To obtain the classifier parameters before these can be used for POI detection module 205, the classifier is trained in a POI detection training module 450 using images 451 with manually annotated POI locations 452. Pre-processed images 451 from patients with marked POI locations 452 in these images may form the input for the training module 450. In certain embodiments, manually marked POI locations can be hand annotated nuclear pixels. Other POI locations may be used consistent with the spirit of the disclosure, for example, manually annotated gland centers, nuclei or gland boundaries or epithelial nuclei centroids determined by automatically analyzing a registered image of the same tissue obtained using another modality such as fluorescent in situ hybridization (FISH).

Training data preparation module 453 samples sub-image windows centered at various locations in the training images 451, and categorizes these windows into positive (POI) and negative (non-POI) sets 454 based on whether their central pixel is a manually annotated POI location or not. In certain embodiments, the mentioned categorization may be nuclear centroids (POI) and other (non-POI) pixel locations, where nuclear centroids are the pixels that lie within manually marked nuclei POI locations and the pixels at non-POI locations are considered as other pixels, for example. Consistent with the spirit of this disclosure, certain embodiments and implementations may extract sub-images of multiple fixed sized windows centered at POI and non-POI locations for positive and negative sets.

In some embodiments, POI classifier training module 455 is a machine learning system or a classifier such as a convolutional neural network with associated parameters such as weights and hyper-parameters such as depth, filter sizes, etc. The sub-images of fixed window size from the training set 454 may be inputted into the convolutional neural network and their respective labels are the desired output. The convolutional neural network may be trained or optimized to minimize a cost function, such as cross-entropy between the correct labels and the neural network predictions by using an optimization method such as gradient descent. The objective of the training or optimization process is to reduce the difference between the classifier output and the known output (POI vs. non-POI status). With sufficient training using example input-output pairs, a machine learning based POI classifier training module learns to predict labels for the central pixel of input sub-image windows of pre-processed tissue image. For POI detection in new patient tissue images, a set of parameters and hyper-parameters 499 of the POI classifier training module 455 are saved in the memory of a computing unit. A validation data set similar to the training data set with pre-processed images along with their known POI locations may be used to ascertain the performance of the POI classifier. If the performance is unsatisfactory on the validation dataset, more training data may be collected, or the architecture (determined by hyper-parameters) of the classifier may be changed.

Consistent with the spirit of this disclosure, one of several machine learning systems such as support vector machines, random forests, penalized logistic regression etc. may be used as a POI classifier training module 455. Additionally, a plethora of optimization techniques and cost functions are available for training various embodiments of the POI detector training module, consistent with the spirit of this disclosure. Further, instead of inputting sub-images, several features including but not limited to texture information, gradient magnitude and direction, color histogram vectors, entropy of gradient directions, graph based features encoding pixel relationships within a sub-image can be extracted from each sub-image and used as input to the POI classifier training module 455.

The embodiments described herein are only illustrative, and other ways of detecting POIs may also be used, including those not based on machine learning, for example fast radial symmetry transform (FRST) to detect nuclei, or scale invariant feature transform (SIFT) or speeded up robust feature transform to detect other points etc. Similarly, in embodiments where machine learning is used, frameworks other than convolutional neural networks may also be used, such as recurrent neural networks, support vector machine, random forests, penalized logistic regression, etc.

Figure 5:
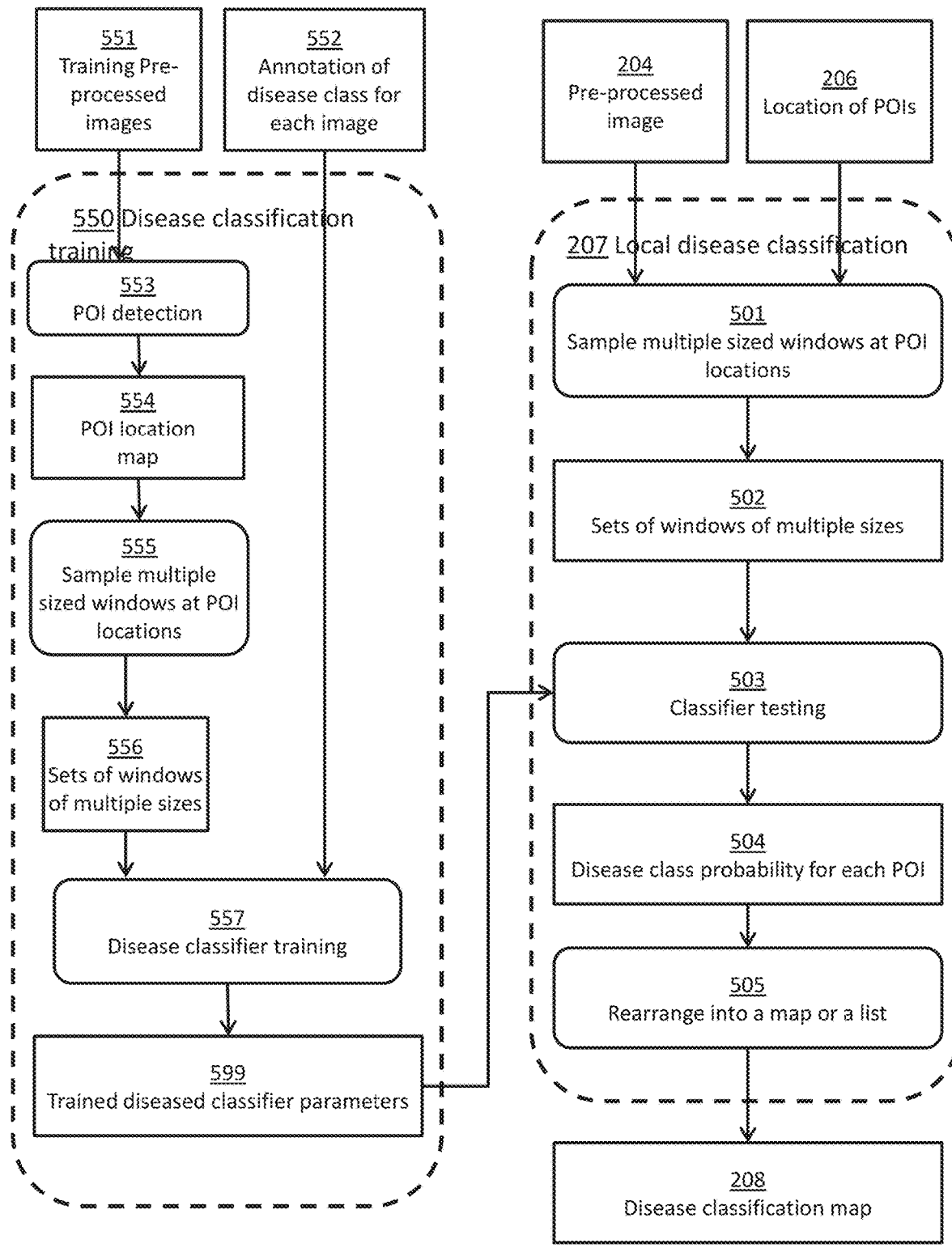
FIG. 5 is an illustration of an exemplary method for disease classification.

FIG. 5 is an illustration of an exemplary method for local disease classification. Within the local disease classification module 207, the input from pre-processed image 204 and the POI location map 206 are taken as input by a module 501 that samples a set of one or more sub-image windows of fixed sizes centered at each POI location 502. If more than one sub-image is sampled at each POI location, then they are of different sizes, usually to capture the visual pattern at different spatial scales. The sets of sub-image windows, where one set is associated with one POI location 502 is input one at a time for ach POI location into a disease classifier module 503, which outputs disease class probability for each disease class at each POI location 504. This classifier may use a set of parameters 599 such as weights of a neural network to compute disease class probabilities. These parameters 599 can be stored on the same computing device as the one that stores disease classification module 207, or may be brought from another computing device through a communication link such as the internet. The disease class probability for each disease class at each POI location may be transformed through a rearrangement operation of one of several types into a disease classification map 208, which is the output of the local disease classification module 207.

To obtain the parameters for classification, a training process is conducted in a separate disease classification training module 550. The training pre-processed images of patients 551, along with their known disease class 552 are input into the training module 550. Within the training module 550, the training pre-processed images 551 are read by a POI detection module 552, which produces a POI location map 554 similar to POI detection module 205. One or more fixed sized sub-image windows are sampled at each POI by a sampling module 555, which produces a set of sub-image windows 556. Such sets of windows 556 from multiple disease classes along with their labels 552 are used by the disease classifier training module 557 to learn the parameters of a disease classifier 599.

Many disease classes and POI types may be used consistently with the spirit of the disclosure. For example, molecular sub-types of cancer such as luminal, basal, and absence thereof can be used to plan specific treatments. Similarly, treatment outcomes determined using years of follow up after specific treatments can be used as classes such as "likely to metastasize after chemotherapy" vs. "unlikely to metastasize after chemotherapy" so that prognostic models that predict treatment effectiveness and disease course can be built. Additionally, patient survival endpoints determined by years of follow up after specific treatments can be used as classes such as "alive" vs. "dead" to develop survival outcome prediction models.

In some embodiments, the disease class of the training image may be given as a label to all window sets extracted centered at every POI in that image. The paired window sets and their labels at each POI location form the training data.

In certain embodiments, the local disease class training module 557 is a machine learning system such as a convolutional neural network with associated parameters such as weights and hyper-parameters such as depth, filter sizes, etc. and an optimization algorithm such as gradient descent with momentum. The sub-images of fixed window size from the training set 556 are input to the neural network and their respective labels are the desired output. The neural network is trained to minimize a cost function, such as cross-entropy between the desired labels and those predicted by the neural network by using an optimization method such as gradient descent. With sufficient training using example input-output pairs, a machine learning based POI detector training module learns to predict labels for input sub-image windows of processed tissue image. The training may be validated using a validation set. If the classification performance on the validation set is not adequate, more training data may be collected, or the hyper-parameters of the classifier be changed before re-training.

Consistent with the spirit of this disclosure, one of several machine learning systems other than neural networks or convolutional neural networks such as support vector machines, random forests, penalized logistic regression etc. may be used as a local disease classifier training module 557. Additionally, one of several optimization techniques and cost functions are available for training various embodiments of the local disease classifier training module, consistent with the spirit of this disclosure. Further, instead of inputting sub-images, several features including but not limited to texture information, gradient magnitude and direction, color histogram vectors, entropy of gradient directions, graph based features encoding pixel relationships within a sub-image can be extracted from each sub-image and used as input to the POI classifier training module 455.

Figure 6:
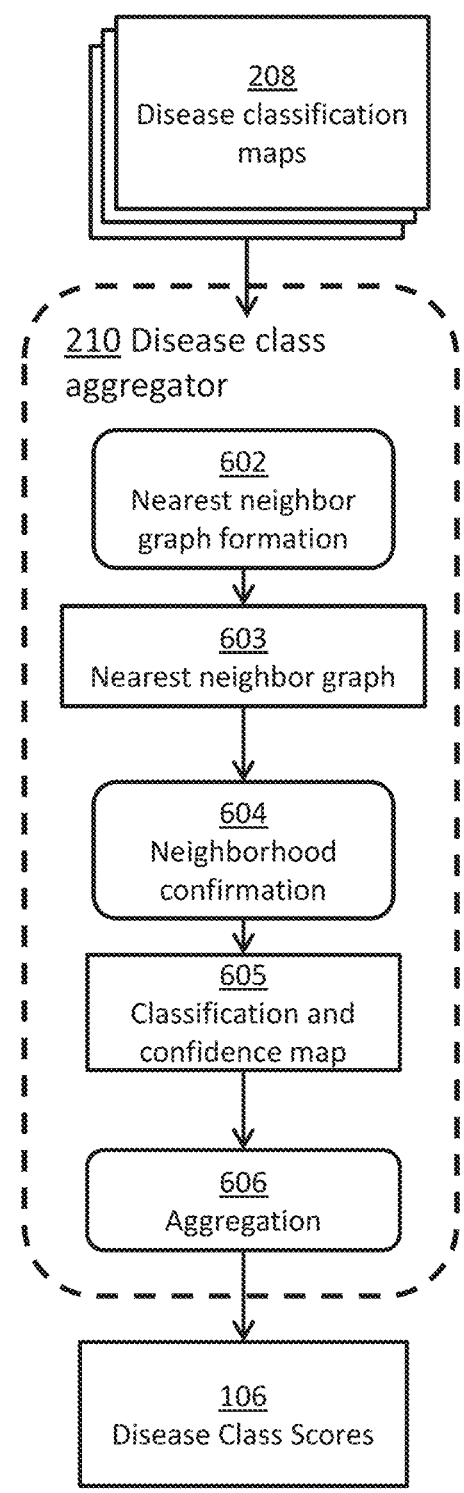
FIG. 6 is an illustration of parts of an exemplary method including aggregation.

FIG. 6 is an illustration of parts of an exemplary method to aggregate local disease class probabilities using disease classification aggregation module 210. The present exemplary method examines the local classifications encoded in disease classification maps 208 and computes confidence in those local classifications for disease classes at each POI across all the tissue images of a patient to produce aggregated disease class scores 106.

In one embodiment, one or more local disease classification maps 208 may be given as input to a nearest neighbor graph formation module 602 within the disease class aggregator 210, which connects two POIs using the edge of a graph 603 if one of them is among the nearest k neighbors, where k is usually around 5. In an example embodiment of the neighborhood confirmation module 604 consistent with the spirit of this disclosure, it examines each vertex or POI in the graph 603 and assigns it a disease class and confidence based on the disease class with highest probability, and whether its nearest neighbor POIs as determined by the edges of the graph 603 have their class in concordance with this POI. This classification and confidence is stored in a classification and confidence map 605. Classification and confidence maps 605 from one or more tissue images of the same patient are examined by the aggregation module 606 to produce disease class scores 106. In an example embodiment of the aggregation module consistent with the spirit of this disclosure, disease class scores are arranged in a matrix whose rows are disease classes, and columns are confidence intervals, while each entry is the percent of POIs across one or more tissue images with that disease classification and confidence equal to or larger than the threshold for that column.

Other embodiments of the disease class aggregation module 210 may also be possible. For example, in one embodiment, the local disease classifications at each POI in disease classification maps 208 may be averaged across POIs for each disease. In another embodiment, the aggregation function 606 itself may be learned using a machine learning technique to produce disease class scores 106 that are advantageous in their utility for planning patient treatment in a way that simple averaging technique may not be.

Figure 7:
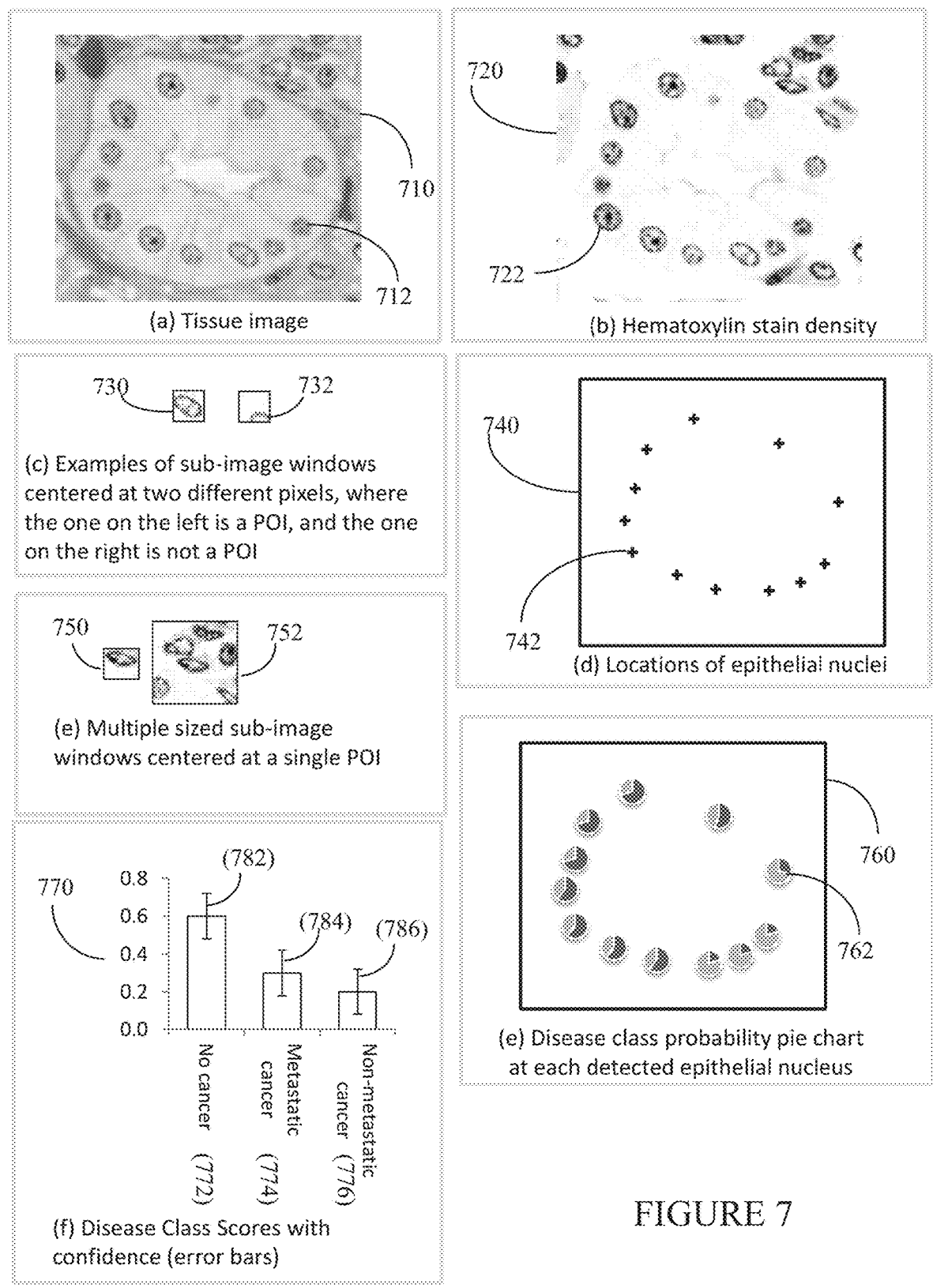
FIG. 7 illustrates exemplary intermediate outputs for one embodiment of the method.

FIG. 7 illustrates exemplary intermediate inputs and outputs in one embodiment of the disease class scoring module 105. An example of a magnified tissue image 710 of a tissue sample stained with hematoxylin and eosin is shown, in which a nucleus 712 is also shown. An exemplary pre-processed image 720 that estimates stain density of hematoxylin (light mean less dense, dark means more dense) is shown along with a nucleus 722. Such a pre-processed image does not suffer from the variations in the actual color of hematoxylin between various labs. From this pre-processed image, POI and non-POI are sampled. A patch centered at a POI 730 and another patch centered at a non-POI 732 are shown. A classifier may finds all POI points in the pre-processed image 722 to help create a POI location map 740, in which location of POI 742 is shown. In this example, the POI is the centroid of an epithelial nucleus. A local disease classification module samples multiple sized sub-image windows 750 and 752 from the pre-processed image 722 using the location map 742. A local disease classifier may take each set of windows centered at each POI and produces disease class probability maps 760, in which a local disease classification probability for a POI is shown as a pie chart 762. Such disease class probability maps can be aggregated using a disease class aggregator module into disease class scores 770, where proportion of POIs representing each disease class 772, 774, 776 (including "no cancer" 772), along with their confidence intervals 782, 784, 786, are shown.

Figure 8:
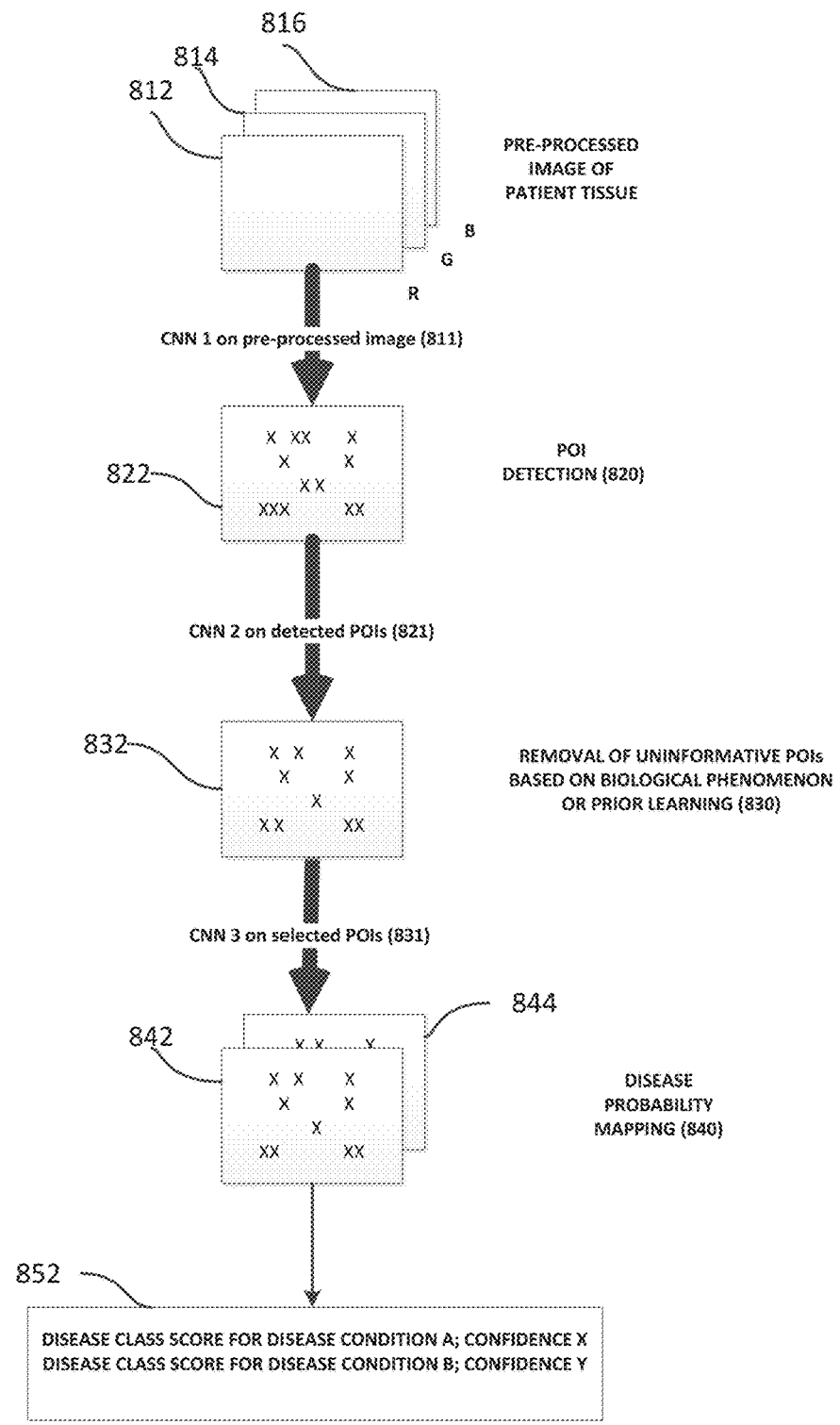
FIG. 8 is an exemplary method including three neural networks.

FIG. 8 is an exemplary method including three convolutional neural networks. In some embodiments, multiple CNNs can be used in tandem to implement a single step of FIG. 2. For example, in FIG. 8, three color channels 812, 814, 816 of a color normalized (pre-processed) image are input into an arrangement of two CNNs 822 and 832 to implement POI detection, such that the first CNN 822 detects all nuclei, and the second CNN 832 discards stromal and adipose nuclei while retaining epithelial nuclei. Then a third CNN 842 takes sub-image windows around epithelial nuclei as input and produces two probability maps 842 and 844, one for each of the two disease classes A and B. Based on these maps, a disease class aggregator module computes their extents and confidences 852.

Figure 9:
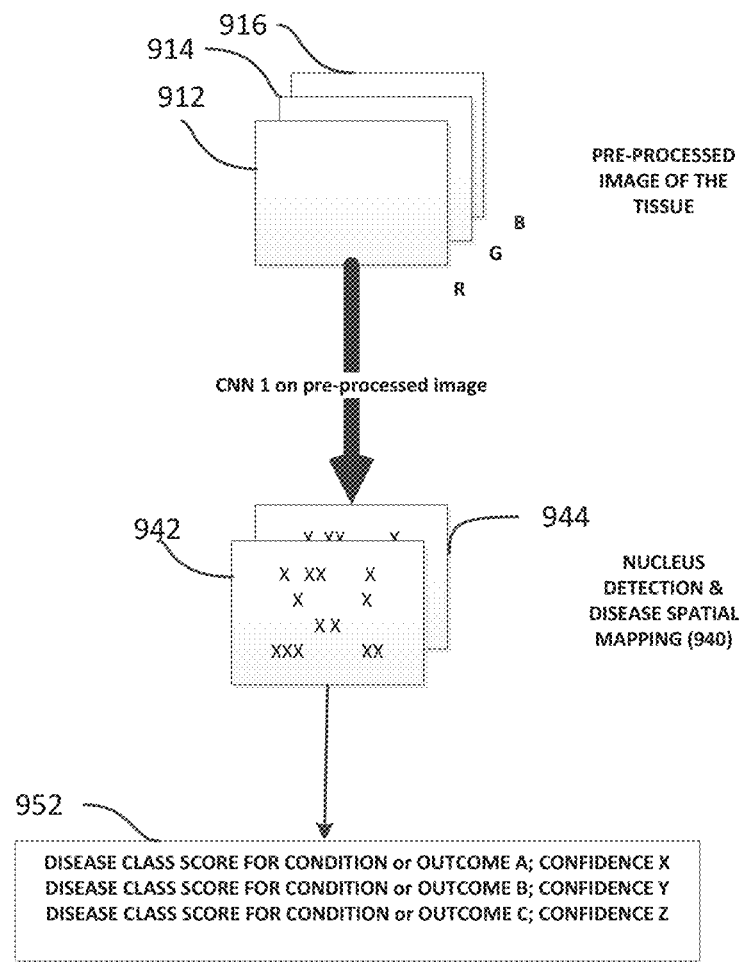
FIG. 9 is an exemplary method including one disease classifier.

FIG. 9 is an exemplary method including one convolutional neural network. In some embodiments of the disease class scoring 105, the steps of pre-processing, detecting POIs, and computing a local disease classification may be done in a single module trained using multi-class label prediction techniques. For example, as shown in FIG. 9, the three color channels 912, 914, 916 of a color normalized (pre-processed) image are input into a single convolutional neural network or CNN (CNN 1), which can be used to examine all possible sub-images of a fixed size, and make a simultaneous decision about whether the point at the center of that sub-image is a POI, and if so, what the probability of each disease class is at that location in form of POI detection and disease class maps 942, 944. These maps can be used by a disease class aggregator module to produce disease class scores 952. In other embodiments, pre-processing may itself take place inside the single CNN.

EXAMPLE 1

Treatment Recommendation

In this example, a team of pathologist and oncologist use the disclosed system to make treatment recommendations for a prostate cancer patient to improve his chance of remission. Three slides of H&E stained biopsy tissue of prostate of a patient with suspected prostate cancer are prepared and scanned using a whole slide scanner to give the three tissue images for that patient. In a computer, each tissue image is color normalized to give a pre-processed image using H&E color prototypes obtained from a different standard image. In a computer, all possible sub-image windows of size 51×51 from each pre-processed image are extracted one by one, and given as an input to a pre-trained deep convolutional neural network to determine if these have an epithelial nucleus centroid at their centers. All pixel locations designated as centroids of epithelial nuclei are points-of-interest (POIs). In another computer, a second pre-trained deep convolutional neural network is used to determine the probability of cancer progression to metastasis if active surveillance (no treatment, but regular follow-up biopsies and blood tests) is chosen as a treatment option. The local disease classifier not only checks that there is prostate cancer at each POI, but also determines the Gleason grade and likelihood of metastasis at each POI. An aggregator module produces disease class scores including percent of POI that look like precursors of those linked to future metastasis, and the confidence in various proportions. Based on this report, the health professionals may determine that although the Gleason grade is low, but the chance of metastasis is high. Therefore, active surveillance is a risky option, and chemotherapy is prescribed.

EXAMPLE 2

Screening & Telemedicine

In this example, we describe the possibility of setting up mobile cancer screening and telemedicine camps made possible through a potential triage embodiment of the our system for populations without access to good healthcare. A mobile screening camp for identifying people at risk for head-and-neck or cervical cancer is organized in a remote village without access to a good hospital or a pathologist. People go to a lab in a van, where their mouth or cervical swabs (PAP smears) are taken by a nurse. A technician stains the tissues with hematoxylin and eosin in another part of the van, and puts it under a microscope attached to a smartphone, wherein the smartphone is an embodiment of both the image capturing component and the computer component described in this disclosure. One of the modules running on the smartphone is used to enter patient details and capture images of the view from the microscope. These images of a patient are passed to the pre-processing module residing in the smartphone. The pre-processing module color-normalizes the images, and passes them to a POI detection module. The POI detection module detects centroids of nuclei using pre-trained parameters of a convolutional neural network with approximately ten layers of artificial neurons because running hundreds of layers requires computing power that is infeasible to be carried in a van lab. The detected POIs and the pre-processed (color-normalized) images are passed to a local disease state classification module that assigns probabilities to each POI being healthy, benign lesion, pre-cancerous, and cancerous. These local classification maps are passed to a module that aggregates these decisions to produce a disease classification report wherein, the patient is either cleared if more than 95% of the POIs are judged benign with more than 70% confidence, or otherwise advised to visit a doctor for further examination. Based on the patient's availability and time slots for pathologists in nearest clinics and hospitals, the technician fixes an appointment for the patient. Upon confirmation of the appointment, the tissue images and the disease classification report of the patient are sent over the mobile or Wi-Fi network to the doctor with whom the appointment was set. Without this system, getting a pathologist to go to the rural area or to examine all patients screened would make such a mass screening program infeasible. For this particular embodiment, the local disease classification module has to be pre-trained with labeled example POI sub-image windows of each class—healthy, benign lesion, pre-cancerous, and cancerous.

EXAMPLE 3

Treatment Planning

In this example, we describe how extra information provided to a pathologist or an oncologist using the disclosed system and methods may be used to develop individualized treatment plans for two patients. Current clinical diagnosis practices would have likely led to the same treatment plan for both. A patient with suspected breast lump checks in to a clinic for a mammogram. The mammogram reveals a potential tumor whose biopsy is taken. The tissue extracted from the biopsy is cut into four adjacent sections and stained with hematoxylin+eosin (H&E), HER2neu, ER, and PR stains respectively. Conventionally, the presence of cancer is ascertained through the microscopic examination of H&E, while the clinical decision making starting from determination of sub-type of cancer to treatment planning is done through the examination of ER, PR, and HER2neu. If the patient is assessed to be a case of 3+ on a scale of 0, 1, 2+, and 3+ in HER2 positivity determined by examination of HER2neu stained tissue, then she is prescribed an anti-HER2 neoadjuvant therapy such as Trastuzumab for six months before a mastectomy operation. About half of such patients show no signs of remaining cancer upon examination of the resected tissue from the operation, while others show increase or decrease in cancer, but not its disappearance. In such a scenario, if the H&E stained biopsy slide was used in our system, whose magnification and image capturing embodiment was a whole slide scanner, while its disease classification module was a remote cloud computer server connected to a computer storing images captured from the whole slide scanner, then more personalized treatment planning could be possible. In this scenario, the H&E image would be pre-processed by the pre-processing module residing in the cloud server, which will estimate the stain densities of hematoxylin and eosin at each pixel in the image of the H&E stained tissue slide. The two stain densities form the pre-processed image, which is input into a POI detection module which runs a pre-trained deep residual network to detect the locations of all the epithelial nuclei as POIs. The POI locations and the stain density maps are input into another module on the cloud server that extracts two windows of size 45×45 and 135×135 each centered at each POI and passes them to a two-stream deep residual network which determines the probabilities of each POI being HER2, luminal A, luminal B, basal-like, or none of these as a local disease classification map. The local disease classification map is input into a disease classification report module that computes a confidence in each local disease classification based on the probability distribution described above and its concordance with disease class probability distribution of nearby POIs. This local disease classification and local disease class confidence is aggregated into a report that computes the percent of POIs for each of the four disease classes HER2, luminal A, luminal B, basal-like, which have confidence above 80%. Based on this report, if the proportion of basal-like tumor is above a threshold, which is an aggressive subtype of tumor, the pathologist orders an EGFR and CK5/6 staining of another section of the patient tissue to confirm the presence of basal-like sub-type. Based on the pathologist's report of the manual tissue visual inspection, and the report generated by the said embodiment of our system, an oncologist decides that the patient needs not just neoadjuvant anti-HER2 therapy but a monthly dose of chemotherapy with doxorubicin until the operation to get rid of basal-like sub-clonal tumor cell population that is also present in addition to HER2-amplified tumor cell population.

EXAMPLE 4

Early Stage Tumor Detection and Pathological Sub-type Identification

In this example, we describe how an embodiment of the present disclosure can be used to process microspectroscopic images of colon tissue for early stage tumor detection and sub-type identification. Most colorectal tumors can be classified into one of the four sub-types viz. normal, hyperplasia, dysplasia and carcinoma in their increasing order of aggressiveness. Numerous studies have reported that early detection, sub-type identification and treatment of an individual colon tumor can improve the survival outcome and patient's quality of life through appropriate treatment recommendations selected on the basis of tumor sub-type. Microspectroscopic images of tissue samples captured using Fourier Transform Infra-Red (FTIR) or Quantum Cascade Laser (QCL) scanners offer molecular specificity of vibration spectroscopy and spatial resolution of optical microscopy without altering the chemical composition of the sample as done by the conventional staining methods such as H&E or IHC staining. As a result, these methods are becoming increasingly popular for detection and assessment of various diseases including colon cancer. A slide of unstained (or untreated) tissue sample of colon of a patient with suspected colon cancer is prepared and scanned using a FTIR scanner to obtain hyperspectral image (HSI) of the tissue that contains 770 spectral bands per pixel. In a computer, the HSI is pre-processed using a band-selection algorithm, such as non-negative matrix factorization (NMF), to identify 20 spectral bands per pixel that represents the spectral characteristics of various colon tissue components such as epithelial cells, non-epithelial Goblet cells, and stroma. In this example, pre-processing module reduces the memory requirements for further processing and improves the accuracy of tumor sub-type detection by selecting clinically relevant bands from the available spectral information at each pixel of an HSI. Each 20-band HSI pixel is given as input to a pre-trained hierarchical clustering based classifier to determine if the pixel belonged to colon epithelium, stroma, non-epithelial Globlet cells or background. The output of the hierarchical clustering based classifier is a tissue component classification map that assigns one of the four labels mentioned above to each pixel location. Noticeably, each tissue component in a patient tissue image serves as a POI in this example. The tissue component classification map is then used to extract features such as area, circumference, length of major and minor axis, parameters of best fit circle, ellipse or polyhedron, graph based features encoding the concordance of labels among neighboring pixels, etc. for each POI in a patient tissue image. These features are then inputted to a pre-trained penalized logistic regression based disease classifier that assigns probabilities to each POI belonging to one of the four sub-types viz. normal, dysplasia, hyperplasia, and carcinoma. This local disease classification at each POI is aggregated into a report that computes the percent of POIs for each of the four sub-types viz. normal, dysplasia, hyperplasia, and carcinoma. Based on the report generated by this embodiment of the present disclosure and pathologist's report based on visual inspection of the adjacent H&E stained tissue sample appropriate treatment selections can be made by an oncologist.

While the embodiments described above are generally directed to a classification of cancers, the present disclosure is not so limited and may be applicable to other diseases such as for detection of pathogens for infectious diseases, cells with genetic defects such as sickle cell anemia. Further, present disclosure is no way limited to conventional tissue slide preparation, staining and imaging protocols but can be adapted for other tissue slide preparation, staining and imaging modalities such as PAP smears and liquid biopsies. Additionally, the utility of the present disclosure can be extended by those skilled in the art to numerous other applications such as land cover assessment, crop health monitoring, urban planning, etc. by processing optical, microwave, or hyper-spectral satellite images according to the embodiments disclosed herein.

Moreover, while specific embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as defined by the following claims.

What is claimed is:

1. A system comprising:
    an imaging apparatus
        operative to capture one or more images of a patient tissue;
    a processor, operatively coupled to the imaging apparatus;
        memory, operatively coupled to the processor; and
        instructions stored in the memory, executable by the processor, that when executed cause the processor to determine one or more disease class scores for a disease state for the patient tissue comprising:
    a pre-processing module operative to apply one or more mathematical functions on the one or more images of the patient tissue to obtain one or more processed images;
    a points-of-interest detection module, operative to locate one or more points-of-interest on the processed images using a point-of-interest detector;
    a classification mapping module, operative to generate one or more disease spatial maps composed of one or more probability metric of disease classifications, wherein one or more disease classifiers are applied to the one or more points-of-interest; and the disease classifier determines the probability metric for one out of two or more disease classes for each point-of-interest; and
    a classification aggregator module operative to determine the disease class scores for each disease classification for each image by combining the one or more probability metric of the one or more disease spatial maps across the one or more points-of-interest located in each of the processed images using an aggregation formula.

2. The system of claim 1, wherein the points-of interest comprise nuclei centers or gland centers.

3. The system of claim 1, wherein the points-of interest are detected proximal to their center points using a point-of-interest detector comprising at least one neural network selected from the group of: a pre-trained neural network, a pre-trained convolutional neural network, a pre-trained recurrent neural network and a pre-trained deep neural network.

4. The system of claim 1, wherein the one or more images of the patient tissue comprises two or more slides of the patient tissue from the same patient.

5. The system of claim 1, wherein the patient tissue has been stained with hematoxylin and eosin (H&E).

6. The system of claim 1, wherein the two or more disease classes comprise cancer types, cancer grades, cancer scores, absence of cancer, cancer sub-types (pathological, molecular or genomic), treatment or survival outcomes as determined by assessment and follow-up by human experts or by genetic sequencing of cells.

7. The system of claim 1, wherein the aggregation formula is applied to all the points-of-interest.

8. The system in claim 1, wherein the aggregation formula is applied to a sub-set of the points-of-interest using an aggregation rule wherein 10 percent of points-of-interest from each disease class are selected for aggregation.

9. The system of claim 1, wherein the aggregation formula is applied to two or more images of the same patient tissue or to two or more images of a plurality of patient tissue from the same patient.

10. The system of claim 1, wherein the one or more probability metric of disease classifications is the score, grade or severity for a disease state.

11. The system of claim 1, wherein the measure of one or more disease classifications is the probability of a cancer sub-type, degree, grade or score.

12. The system in claim 1, wherein the imaging apparatus comprises a whole-slide imaging scanning equipment and the patient tissue is fixed on one or more slides.

13. The system in claim 1, wherein the imaging apparatus comprises a microscope with optical zoom and a camera for capturing the one or more images of the patient tissue.

14. A method for determining one or more disease class scores of a disease state on a patient tissue:
    inputting one or more images of the patient tissue, wherein the tissue has been treated with a stain comprising one or more stain components;
    generating a processed image from the images of the patient tissue;
    locating one or more points of interest in the processed image using a first classifier;
    generating a disease spatial map with the probability of a disease state at the points-of-interest in the tissue image by using a second classifier; and
    aggregating the probability of the disease state at each point-of-interest located to obtain the disease class scores of the disease state for the patient tissue.

15. The method of claim 14, wherein locating one or more points of interest in the processed image using a first classifier, comprises:
    using a nucleus detector, as the first classifier, the nucleus detector comprising at least one neural network selected from the group of: a pre-trained neural network and a convolutional neural network.

16. The method of claim 14, further comprising:
    aggregating the probability of the disease state from two or more images of the patient tissue from the same patient.

17. A non-transitory computer readable medium having a series of instructions that, when executed by a processor, cause the processor to:
    input one or more images of the patient tissue, wherein the tissue has been treated with a stain comprising two or more stain components;
    locate one or more points of interest in the one or more images of the patient tissue using a first classifier;

generate a disease spatial map with the probability of a disease state at one or more points-of-interest by using a combined classifier into one out of two or more disease classes; and aggregate the probability of the disease state at each point-of-interest to obtain one or more disease class scores of the disease state for the patient tissue.

18. The medium of claim 17, wherein the series of instructions further cause the processor to:

perform stain separation on the one more images of the patient tissue.

19. The medium of claim 17, wherein the series of instructions further cause the processor to:

generate the disease spatial map where the one or more points-of-interest are nuclei detected at their center points; and determine by using the combined classifier, the probability of a disease state at the detected nuclei.

20. The medium of claim 17, wherein the series of instructions further cause the processor to: use a pre-trained convolutional neural network as the combined classifier.

* * * * *